US010534129B2

(12) United States Patent
Tearney et al.

(10) Patent No.: US 10,534,129 B2
(45) Date of Patent: Jan. 14, 2020

(54) SYSTEM AND METHOD PROVIDING INTRACORONARY LASER SPECKLE IMAGING FOR THE DETECTION OF VULNERABLE PLAQUE

(75) Inventors: Guillermo J. Tearney, Cambridge, MA (US); Seemantini K. Nadkarni, Boston, MA (US); Brett Eugene Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 279 days.

(21) Appl. No.: 12/058,279

(22) Filed: Mar. 28, 2008

(65) Prior Publication Data
US 2008/0262359 A1 Oct. 23, 2008

Related U.S. Application Data

(60) Provisional application No. 60/909,288, filed on Mar. 30, 2007.

(51) Int. Cl.
| | |
|---|---|
| *G02B 6/04* | (2006.01) |
| *G02B 6/06* | (2006.01) |
| *A61B 1/00* | (2006.01) |
| *A61B 5/00* | (2006.01) |
| *G02B 6/32* | (2006.01) |

(52) U.S. Cl.
CPC ............ *G02B 6/06* (2013.01); *A61B 1/00096* (2013.01); *A61B 1/00167* (2013.01); *A61B 5/0066* (2013.01); *A61B 5/0084* (2013.01); *A61B 5/7285* (2013.01); *G02B 6/32* (2013.01)

(58) Field of Classification Search
USPC .................................................. 600/476, 478
See application file for complete search history.

(56) References Cited

U.S. PATENT DOCUMENTS

| | | |
|---|---|---|
| 2,339,754 A | 1/1944 | Brace |
| 3,090,753 A | 5/1963 | Matuszak et al. |
| (Continued) | | |

FOREIGN PATENT DOCUMENTS

| | | |
|---|---|---|
| CN | 1550203 | 12/2004 |
| DE | 4105221 | 9/1991 |
| (Continued) | | |

OTHER PUBLICATIONS

Japanese Office Action dated Dec. 2, 2008.
(Continued)

*Primary Examiner* — Joseph M Santos Rodriguez
(74) *Attorney, Agent, or Firm* — Quarles & Brady LLP

(57) ABSTRACT

Apparatus and method according to an exemplary embodiment of the present invention can be provided for analyzing tissue. For example, the apparatus can include at least one first arrangement configured to illuminate at least one anatomical structure with at least one of at least one electromagnetic radiation. The apparatus can also include at least one second arrangement that may include at least two wave-guiding arrangements associated with one another that are configured to receive a further electro-magnetic radiation reflected from the tissue and transmit at least one speckle pattern associated with the further electro-magnetic radiation. The wave-guiding arrangements may be structured so as to reduce crosstalk therebetween.

35 Claims, 21 Drawing Sheets

(56) References Cited

U.S. PATENT DOCUMENTS

| | | |
|---|---|---|
| 3,601,480 A | 8/1971 | Randall |
| 3,674,452 A * | 7/1972 | Strak .................... G02B 23/26 385/116 |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A * | 3/1994 | Alfano et al. .................. 600/475 |
| 5,293,873 A | 3/1994 | Fang |
| 5,302,025 A | 4/1994 | Kleinerman |
| 5,304,173 A * | 4/1994 | Kittrell et al. .................. 606/15 |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,404,415 A | 4/1995 | Mori et al. |
| 5,411,016 A | 5/1995 | Kume et al. |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Gunderson et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,807,264 A * | 9/1998 | Paltieli ....................... 600/477 |
| 5,810,719 A | 9/1998 | Toida |
| 5,817,144 A | 10/1998 | Kenton et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |

(56) References Cited

U.S. PATENT DOCUMENTS

| | | |
|---|---|---|
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | De Boer et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 * | 3/2001 | Clarke .......................... 600/476 |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 * | 5/2002 | Everett et al. ................ 356/336 |
| 6,389,307 B1 * | 5/2002 | Abela .......................... 600/478 |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | De Boer et al. |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |

(56) References Cited

U.S. PATENT DOCUMENTS

| | | |
|---|---|---|
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,263,261 B2 * | 8/2007 | Henze et al. ............... 385/115 |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Tearney et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Yun |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Rox et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183601 A1 * | 12/2002 | Tearney ............. A61B 1/00082 600/310 |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0045778 A1 * | 3/2003 | Ohline ............... A61B 1/0053 600/114 |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0120156 A1 * | 6/2003 | Forrester et al. ............. 600/473 |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0212394 A1 * | 11/2003 | Pearson ............ A61B 18/1477 606/41 |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0001662 A1 * | 1/2004 | Wong .................. A61B 5/1101 385/15 |
| 2004/0002650 A1 | 1/2004 | Mandrusov et al. |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0190844 A1 * | 9/2004 | Boyd .................. H04N 1/1013 385/120 |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0185192 A1 * | 8/2005 | Kim .................. A61B 5/0066 356/497 |
| 2005/0190372 A1 | 9/2005 | Dogariu et al. |
| 2005/0197530 A1 | 9/2005 | Wallace et al. |
| 2005/0221270 A1 | 10/2005 | Connelly et al. |
| 2005/0254061 A1 | 11/2005 | Alphonse et al. |

(56) References Cited

U.S. PATENT DOCUMENTS

| | | | |
|---|---|---|---|
| 2005/0259934 A1* | 11/2005 | Temelkuran | A61B 1/0017 385/125 |
| 2006/0020172 A1 | 1/2006 | Luerssen et al. | |
| 2006/0033923 A1 | 2/2006 | Hirasawa et al. | |
| 2006/0039004 A1 | 2/2006 | de Boer et al. | |
| 2006/0093276 A1 | 5/2006 | Bouma et al. | |
| 2006/0103850 A1 | 5/2006 | Alphonse et al. | |
| 2006/0106375 A1 | 5/2006 | Werneth et al. | |
| 2006/0146339 A1 | 7/2006 | Fujita et al. | |
| 2006/0155193 A1 | 7/2006 | Leonardi et al. | |
| 2006/0164639 A1 | 7/2006 | Horn et al. | |
| 2006/0167363 A1 | 7/2006 | Osypka et al. | |
| 2006/0171503 A1 | 8/2006 | O'Hara et al. | |
| 2006/0184048 A1 | 8/2006 | Saadat et al. | |
| 2006/0193352 A1 | 8/2006 | Chong et al. | |
| 2006/0224053 A1 | 10/2006 | Black et al. | |
| 2006/0244973 A1 | 11/2006 | Yun et al. | |
| 2006/0279742 A1 | 12/2006 | Tearney | |
| 2007/0002435 A1 | 1/2007 | Ye et al. | |
| 2007/0019208 A1 | 1/2007 | Toida et al. | |
| 2007/0038040 A1 | 2/2007 | Cense et al. | |
| 2007/0070496 A1 | 3/2007 | Gweon et al. | |
| 2007/0076217 A1 | 4/2007 | Baker et al. | |
| 2007/0078500 A1* | 4/2007 | Ryan et al. | 607/88 |
| 2007/0086013 A1 | 4/2007 | De Lega et al. | |
| 2007/0086017 A1 | 4/2007 | Buckland et al. | |
| 2007/0091317 A1 | 4/2007 | Freischlad et al. | |
| 2007/0133002 A1 | 6/2007 | Wax et al. | |
| 2007/0188855 A1 | 8/2007 | Milen et al. | |
| 2007/0208225 A1 | 9/2007 | Czaniera et al. | |
| 2007/0208257 A1* | 9/2007 | Furnish | A61B 5/6853 600/479 |
| 2007/0223006 A1 | 9/2007 | Tearney et al. | |
| 2007/0233056 A1 | 10/2007 | Yun | |
| 2007/0233396 A1 | 10/2007 | Tearney et al. | |
| 2007/0236700 A1 | 10/2007 | Yun et al. | |
| 2007/0258094 A1 | 11/2007 | Izatt et al. | |
| 2007/0291277 A1 | 12/2007 | Everett et al. | |
| 2008/0002197 A1 | 1/2008 | Sun et al. | |
| 2008/0007734 A1 | 1/2008 | Park et al. | |
| 2008/0021275 A1 | 1/2008 | Tearney et al. | |
| 2008/0049220 A1 | 2/2008 | Izzia et al. | |
| 2008/0094613 A1 | 4/2008 | de Boer et al. | |
| 2008/0094637 A1 | 4/2008 | de Boer et al. | |
| 2008/0097225 A1 | 4/2008 | Milen et al. | |
| 2008/0097709 A1 | 4/2008 | de Boer et al. | |
| 2008/0100837 A1 | 5/2008 | de Boer et al. | |
| 2008/0152353 A1 | 6/2008 | de Boer et al. | |
| 2008/0154090 A1 | 6/2008 | Hashimshony | |
| 2008/0192236 A1 | 8/2008 | Smith et al. | |
| 2008/0204762 A1 | 8/2008 | Izatt et al. | |
| 2008/0214927 A1* | 9/2008 | Cherry | G01R 33/481 600/411 |
| 2008/0228086 A1 | 9/2008 | Ilegbusi | |
| 2008/0234560 A1 | 9/2008 | Nomoto et al. | |
| 2008/0265130 A1 | 10/2008 | Colomb et al. | |
| 2008/0308730 A1 | 12/2008 | Vizi et al. | |
| 2009/0005691 A1 | 1/2009 | Huang | |
| 2009/0011948 A1 | 1/2009 | Unlu et al. | |
| 2009/0051923 A1 | 2/2009 | Zuluaga | |
| 2009/0131801 A1 | 5/2009 | Suter et al. | |
| 2009/0192358 A1 | 7/2009 | Yun | |
| 2009/0196477 A1 | 8/2009 | Cense et al. | |
| 2009/0273777 A1 | 11/2009 | Yun et al. | |
| 2009/0281390 A1 | 11/2009 | Quinjun et al. | |
| 2009/0290156 A1 | 11/2009 | Popescu et al. | |
| 2009/0305309 A1 | 12/2009 | Chien et al. | |
| 2010/0002241 A1 | 1/2010 | Hirose | |
| 2010/0086251 A1 | 4/2010 | Xu et al. | |
| 2010/0094576 A1 | 4/2010 | de Boer et al. | |
| 2010/0150467 A1 | 6/2010 | Zhao et al. | |

FOREIGN PATENT DOCUMENTS

| | | |
|---|---|---|
| DE | 4309056 | 9/1994 |
| DE | 19542955 | 5/1997 |
| DE | 10351319 | 6/2006 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 62-188001 | 6/1989 |
| JP | 04-056907 | 2/1992 |
| JP | 20040056907 | 2/1992 |
| JP | 4135550 | 5/1992 |
| JP | 4135551 | 5/1992 |
| JP | 5509417 | 11/1993 |
| JP | 9-230248 | 9/1997 |
| JP | 10-267631 | 10/1998 |
| JP | 2000-046729 | 2/2000 |
| JP | 2000-121961 | 4/2000 |
| JP | 2000-504234 | 4/2000 |
| JP | 2001-174404 | 6/2001 |
| JP | 2001-174744 | 6/2001 |
| JP | 2001-508340 | 6/2001 |
| JP | 2007-539336 | 6/2001 |
| JP | 2001-212086 | 8/2001 |
| JP | 2001-525580 | 12/2001 |
| JP | 2002-205434 | 2/2002 |
| JP | 2002-095663 | 4/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2005-062850 | 3/2005 |
| JP | 2005-110208 | 4/2005 |
| JP | 2005-195485 | 7/2005 |
| JP | 2007271761 | 10/2007 |
| JP | 2003-102672 | 4/2012 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 1998048846 | 11/1998 |
| WO | 9905487 | 2/1999 |
| WO | 1999044089 | 2/1999 |
| WO | 9944089 | 9/1999 |
| WO | 1999-45338 | 10/1999 |
| WO | 9957507 | 11/1999 |
| WO | 2000-42906 | 7/2000 |
| WO | 0058766 | 10/2000 |
| WO | 0101111 | 1/2001 |
| WO | 0108579 | 2/2001 |
| WO | 2001027679 | 4/2001 |
| WO | 0138820 | 5/2001 |
| WO | 0142735 | 6/2001 |

(56) References Cited

FOREIGN PATENT DOCUMENTS

| WO | 0236015 | 5/2002 |
|---|---|---|
| WO | 0238040 | 5/2002 |
| WO | 20020037075 | 5/2002 |
| WO | 0254027 | 7/2002 |
| WO | 2002053050 | 7/2002 |
| WO | 2002-083003 | 10/2002 |
| WO | 2002084263 | 10/2002 |
| WO | 2003-012405 | 2/2003 |
| WO | 20030013624 | 2/2003 |
| WO | 03020119 | 3/2003 |
| WO | 03052478 | 6/2003 |
| WO | 2003046495 | 6/2003 |
| WO | 2003046636 | 6/2003 |
| WO | 03062802 | 7/2003 |
| WO | 2003062802 | 7/2003 |
| WO | 20030053226 | 7/2003 |
| WO | 03-088826 | 10/2003 |
| WO | 2003105678 | 12/2003 |
| WO | 2004034869 | 4/2004 |
| WO | 2004-043251 | 5/2004 |
| WO | 2004057266 | 7/2004 |
| WO | 20040066824 | 8/2004 |
| WO | 2004088361 | 10/2004 |
| WO | 04105598 | 12/2004 |
| WO | 20050000115 | 1/2005 |
| WO | 2005047813 | 5/2005 |
| WO | 2005054780 | 6/2005 |
| WO | 2005082225 | 9/2005 |
| WO | 20050082225 | 9/2005 |
| WO | 2006004743 | 1/2006 |
| WO | 2006014392 | 2/2006 |
| WO | 2006039091 | 4/2006 |
| WO | 20060038876 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007083138 | 7/2007 |
| WO | 2007084995 | 7/2007 |
| WO | 20090153929 | 12/2009 |
| WO | 2011-055376 | 5/2011 |

OTHER PUBLICATIONS

International Search Report and Written Opinion dated Feb. 24, 2009 for PCT/US2008/076447.
European Official Communication dated Feb. 12, 2008 for EP 07718117.0.
International Search Report and Written Opinion dated Jun. 10, 2009 for PCT/US2008/075456.
European Search Report dated May 5, 2009 for European Application No. 01991471.2.
Notice of Reasons for Rejection dated Jul. 14, 2009 for Japanese Application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
International Search Report and Written Opinion dated Dec. 23, 2009.
Office Action dated Dec. 9, 2008 for U.S. Appl. No. 09/709,162.
Office Action dated Dec. 23, 2008 for U.S. Appl. No. 11/780,261.
Office Action dated Jan. 9, 2009 for U.S. Appl. No. 11/624,455.
Office Action dated Feb. 18, 2009 for U.S. Appl. No. 11/285,301.
Office Action dated Feb. 18, 2009 for U.S. Appl. No. 11/697,012.
Office Action dated Feb. 23, 2009 for U.S. Appl. No. 11/956,129.
Office Action dated Mar. 16, 2009 for U.S. Appl. No. 11/621,694.
Office Action dated Mar. 24, 2009 for U.S. Appl. No. 11/744,412.
Office Action dated Oct. 1, 2009 for U.S. Appl. No. 11/677,278.
Office Action dated Oct. 6, 2009 for U.S. Appl. No. 12/015,642.
Summons to attend Oral Proceedings for European Patent No. 06813365.1 dated Oct. 9, 2009.
Office Action dated Dec. 14, 2009 for U.S. Appl. No. 11/537,123.
Office Action dated Dec. 15, 2009 for U.S. Appl. No. 11/549,397.
Liptak David C. et al., (2007) "On the Development of a Confocal Rayleigh-Brillouin Microscope" *American Institute of Physics* vol. 78, 016106.
Office Action dated Oct. 1, 2008 for U.S. Appl. No. 11/955,986.
Invitation of Pay Additional Fees dated Aug. 7, 2008 for International Application No. PCT/US2008/062354.
Invitation of Pay Additional Fees dated Jul. 20, 2008 for International Application No. PCT/US2007/081982.
International Search Report and Written Opinion dated Mar. 7, 2006 for PCT/US2005/035711.
International Search Report and Written Opinion dated Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion dated Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report dated May 27, 2008 for Australian patent application No. 2003210669.
Notice of Allowance dated Jun. 4, 2008 for U.S. Appl. No. 11/174,425.
European communication dated May 15, 2008 for European patent application No. 05819917.5.
International Search Report and Written Opinion dated Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers—Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".

(56) References Cited

OTHER PUBLICATIONS

Database Biosis Biosciences Information Service, Philadelphia, PA, US; Oct. 2006, Yelin D. et al: "Three-Dimensional Miniature Endoscopy".
International Search Report and Written Opinion dated Mar. 14, 2005 for PCT/US2004/018045.
Notification of the international Preliminary Report on Patentability dated Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Gratin and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection dated Dec. 2, 2008 for Japanese patent application No. 2000-533782.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Jan. 9, 2010 for U.S. Appl. No. 11/624,455.

Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Zhang et al, (Sep. 2004), "Fourier Domain Functional Optical Coherence Tomography", Saratov Fall Meeting 2004, pp. 8-14.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
International Search Report for Application No. PCT/US2007/068233.
International Search Report for Application No. PCT/US2007/060787.
International Search Report and Written Opinion for Application No. PCT/US2007/061463 dated Jan. 23, 2008.
Fujimoto et al., "High Resolution in Vivo Intra-Arterial Imaging with Optical Coherence Tomography," *Official Journal of the British Cardiac Society*, vol. 82, pp. 128-133 Heart, 1999.
D. Huang et al., "Optical Coherence Tomography," *Science*, vol. 254, pp. 1178-1181, Nov. 1991.
Tearney et al., "High-Speed Phase—and Group Delay Scanning with a Grating Based Phase Control Delay Line," *Optics Letters*, vol. 22, pp. 1811-1813, Dec. 1997.
Rollins, et al., "In Vivo Video Rate Optical Coherence Tomography," *Optics Express*, vol. 3, pp. 219-229, Sep. 1998
Saxer, et al., High Speed Fiber-Based Polarization-Sensitive Optical Coherence Tomography of in Vivo Human Skin, *Optical Society of America*, vol. 25, pp. 1355-1357, Sep. 2000.
Oscar Eduardo Martinez, "3000 Times Grating Compress or with Positive Group Velocity Dispersion," *IEEE*, vol. QE-23, pp.59-64, Jan. 1987.
Kulkarni, et al., "Image Enhancement in Optical Coherence Tomography Using Deconvolution," *Electronics Letters*, vol. 33, pp. 1365-1367, Jul. 1997.
Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Images," *Journal of Biomedical Optics*, vol. 4, pp. 125-136, Jan. 1999.
Tearney, et al., "In Vivo Endoscopic Optical Biopsy with Optical Coherence Tomography," *Science*, vol. 276, Jun. 1997.
W. Drexler et al., "In Vivo Ultrahigh-Resolution Optical Coherence Tomography," *Optics Letters* vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.
Agrawal, G.P., "Population Pulsations and Nondegenerate 4-Wave Mixing in Semiconductor—Lasers and Amplifiers," *Journal of the Optical Society of America B—Optical Physics*, vol.5, pp. 147-159, Jan. 1998.
Andretzky, P. et al., "Optical Coherence Tomography by Spectral Radar: Improvement of Signal-to-Noise Ratio," *The International Society for Optical Engineering*, USA, vol. 3915, 2000.
Ballif, J. et al., "Rapid and Scalable Scans at 21 m/s in optical Low-Coherence Reflectometry," *Optics Letters*, vol. 22, pp. 757-759, Jun. 1997.
Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.
Beaud, P. et al., "Optical Reflectometry with Micrometer Resolution for the Investigation of Integrated Optical-Devices," *Leee Journal of Quantum Electronics*, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

(56) References Cited

OTHER PUBLICATIONS

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B—Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A—Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., " 'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A—Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1—Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B—Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

(56) References Cited

OTHER PUBLICATIONS

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—a New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, for No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, with vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002,vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

(56) References Cited

OTHER PUBLICATIONS

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of in Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Material Characterisation and Strain-Field Mapping," *Applied Physics A 76, Materials Science & Processing*, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin in Vivo," 2004, *Optical Society of America*.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., "Comment on Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc.* 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.
Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

(56) References Cited

OTHER PUBLICATIONS

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Acioli, L. H., M. Ulman, et al. (1991). "Femtosecond Temporal Encoding in Barium-Titanate." *Optics Letters* 16(24): 1984-1986.
Aigouy, L., A. Lahrech, et al. (1999). "Polarization effects in apertureless scanning near-field optical microscopy: an experimental study." *Optics Letters* 24(4): 187-189.
Akiba, M., K. P. Chan, et al. (2003). "Full-field optical coherence tomography by two-dimensional heterodyne detection with a pair of CCD cameras." *Optics Letters* 28(10): 816-818.
Akkin, T., D. P. Dave, et al. (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensitivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.
Antcliff, R. J., T. J. ffytche, et al. (2000). "Optical coherence tomography of melanocytoma." *American Journal of Ophthalmology* 130(6): 845-7.
Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.
Anvari, B., T. E. Milner, et al. (1995). "Selective Cooling of Biological Tissues—Application for Thermally Mediated Therapeutic Procedures." *Physics in Medicine and Biology* 40(2): 241-252.
Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks."*Physics in Medicine and Biology* 40(9): 1451-1465.
Arend, O., M. Ruffer, et al. (2000). "Macular circulation in patients with diabetes mellitus with and without arterial hypertension." *British Journal of Ophthalmology* 84(12): 1392-1396.
Arimoto, H. and Y. Ohtsuka (1997). "Measurements of the complex degree of spectral coherence by use of a wave-front-folded interferometer."*Optics Letters* 22(13): 958-960.
Azzolini, C., F. Patelli, et al. (2001). "Correlation between optical coherence tomography data and biomicroscopic interpretation of idiopathic macular hole." *American Journal of Ophthalmology* 132(3): 348-55.
Baba, T., K. Ohno-Matsui, et al. (2002). "Optical coherence tomography of choroidal neovascularization in high myopia." *Acta Ophthalmologica Scandinavica* 80(1): 82-7.
Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE* , 2925: p. 298-303.
Baney, D. M. and W. V. Sorin (1993). "Extended-Range Optical Low-Coherence Reflectometry Using a Recirculating Delay Technique." *Ieee Photonics Technology Letters* 5(9): 1109-1112.
Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.
Barakat, R. (1993). "Analytic Proofs of the Arago-Fresnel Laws for the Interference of Polarized-Light." *Journal of the Optical Society of America a—Optics Image Science and Vision* 10(1): 180-185.
Barbastathis, G. and D. J. Brady (1999). "Multidimensional tomographic imaging using volume holography." *Proceedings of the Ieee* 87(12): 2098-2120.
Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.
Barsky, S. H., S. Rosen, et al. (1980). "Nature and Evolution of Port Wine Stains—Computer-Assisted Study." *Journal of Investigative Dermatology* 74(3): 154-157.
Barton, J. K., J. A. Izatt, et al. (1999). "Three-dimensional reconstruction of blood vessels from in vivo color Doppler optical coherence tomography images." *Dermatology* 198(4): 355-361.
Barton, J. K., A. Rollins, et al. (2001). "Photothermal coagulation of blood vessels: a comparison of high-speed optical coherence tomography and numerical modelling." *Physics in Medicine and Biology* 46.
Barton, J. K., A. J. Welch, et al. (1998). "Investigating pulsed dye laser-blood vessel interaction with color Doppler optical coherence tomography." *Optics Express* 3.
Bashkansky, M., M. D. Duncan, et al. (1997). "Subsurface defect detection in ceramics by high-speed high-resolution optical coherent tomography." *Optics Letters* 22 (1): 61-63.
Bashkansky, M. and J. Reintjes (2000). "Statistics and reduction of speckle in optical coherence tomography." *Optics Letters* 25(8): 545-547.
Baumgartner, A., S. Dichtl, et al. (2000). "Polarization-sensitive optical coherence tomography of dental structures." *Caries Research* 34(1): 59-69.
Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.
Baumgartner, A., C. K. Hitzenberger, et al. (1998). "Signal and resolution enhancements in dual beam optical coherence tomography of the human eye." *Journal of Biomedical Optics* 3(1): 45-54.
Beaurepaire, E., P. Gleyzes, et at. (1998). *Optical coherence microscopy for the in-depth study of biological structures: System based on a parallel detection scheme*, Proceedings of SPIE—The International Society for Optical Engineering.
Beaurepaire, E., L. Moreaux, et al. (1999). "Combined scanning optical coherence and two-photon-excited fluorescence microscopy." *Optics Letters* 24(14): 969-971.
Bechara, F. G., T. Gambichler, et al. (2004). "Histomorphologic correlation with routine histology and optical coherence tomography." *Skin Research and Technology* 10 (3): 169-173.
Bechmann, M., M. J. Thiel, et al. (2000). "Central corneal thickness determined with optical coherence tomography in various types of glaucoma. [see comments]." *British Journal of Ophthalmology* 84(11): 1233-7.
Bek, T. and M. Kandi (2000). "Quantitative anomaloscopy and optical coherence tomography scanning in central serous chorioretinopathy." *Acta Ophthalmologica Scandinavica* 78(6): 632-7.
Benoit, A. M., K. Naoun, et al. (2001). "Linear dichroism of the retinal nerve fiber layer expressed with Mueller matrices." *Applied Optics* 40(4): 565-569.
Bicout, D., C. Brosseau, et al. (1994). "Depolarization of Multiply Scattered Waves by Spherical Diffusers—Influence of the Size Parameter." *Physical Review* E 49(2): 1767-1770.
Blanchot, L., M. Lebec, et al. (1997). *Low-coherence in depth microscopy for biological tissues imaging: Design of a real time control system*. Proceedings of SPIE—The International Society for Optical Engineering.
Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

(56) References Cited

OTHER PUBLICATIONS

Blumenthal, E. Z., J. M. Williams, et al. (2000). "Reproducibility of nerve fiber layer thickness measurements by use of optical coherence tomography." *Ophthalmology* 107(12): 2278-82.
Boppart, S. A., B. E. Bouma, et al. (1996). "Imaging developing neural morphology using optical coherence tomography." *Journal of Neuroscience Methods* 70.
Boppart, S. A., B. E. Bouma, et al. (1997). "Forward-imaging instruments for optical coherence tomography." *Optics Letters* 22.
Boppart, S. A., B. E. Bouma, et al. (1998). "Intraoperative assessment of microsurgery with three-dimensional optical coherence tomography." *Radiology* 208: 81-86.
Boppart, S. A., J. Herrmann, et al. (1999). "High-resolution optical coherence tomography-guided laser ablation of surgical tissue." *Journal of Surgical Research* 82(2): 275-84.
Bouma, B. E. and J. G. Fujimoto (1996). "Compact Kerr-lens mode-locked resonators." *Optics Letters* 21. 134-136.
Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.
Bouma, B. E., M. Ramaswamy-Paye, et al. (1997). "Compact resonator designs for mode-locked solid-state lasers." *Applied Physics B (Lasers and Optics)* B65. 213-220.
Bouma, B. E. and G. J. Teamey (2002). "Clinical imaging with optical coherence tomography." *Academic Radiology* 9(8): 942-953.
Bouma, B. E., G. J. Tearney, et al. (1996). "Self-phase-modulated Kerr-lens mode-locked Cr:forsterite laser source for optical coherence tomography." *Optics Letters* 21(22): 1839.
Bouma, B. E., G. J. Tearney, et al. (2000). "High-resolution imaging of the human esophagus and stomach in vivo using optical coherence tomography." *Gastrointestinal Endoscopy* 51(4): 467-474.
Bouma, B. E., G. J. Tearney, et al. (2003). "Evaluation of intracoronary stenting by intravascular optical coherence tomography." *Heart* 89(3): 317-320.
Bourquin, S., V. Monterosso, et al. (2000). "Video-rate optical low-coherence reflectometry based on a linear smart detector array." *Optics Letters* 25(2): 102-104.
Bourquin, S., P. Seitz, et al. (2001). "Optical coherence topography based on a two-dimensional smart detector array." *Optics Letters* 26(8): 512-514.
Bouzid, A., M. A. G. Abushagur, et al. (1995). "Fiber-optic four-detector polarimeter." *Optics Communications* 118(3-4): 329-334.
Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.
Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.
Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.
Brand, S., J. M. Poneros, et al. (2000). "Optical coherence tomography in the gastrointestinal tract." *Endoscopy* 32(10): 796-803.
Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.
Brezinski, M. E., G. J. Tearney, et al. (1996). "Imaging of coronary artery microstructure (in vitro) with optical coherence tomography." *American Journal of Cardiology* 77 (1): 92-93.
Brezinski, M. E., G. J. Tearney, et al. (1996). "Optical coherence tomography for optical biopsy—Properties and demonstration of vascular pathology." *Circulation* 93(6): 1206-1213.
Brezinski, M. E., G. J. Tearney, et al. (1997). "Assessing atherosclerotic plaque morphology: Comparison of optical coherence tomography and high frequency intravascular ultrasound." *Heart* 77(5): 397-403.
Brink, H. B. K. and G. J. Vanblokland (1988). "Birefringence of the Human Foveal Area Assessed Invivo with Mueller-Matrix Ellipsometry." *Journal of the Optical Society of America a—Optics Image Science and Vision* 5(1): 49-57.
Brosseau, C. and D. Bicout (1994). "Entropy Production in Multiple-Scattering of Light by a Spatially Random Medium." *Physical Review E* 50(6): 4997-5005.
Burgoyne, C. F., D. E. Mercante, et al. (2002). "Change detection in regional and volumetric disc parameters using longitudinal confocal scanning laser tomography." *Ophthalmology* 109(3): 455-66.
Candido, R. and T. J. Allen (2002). "Haemodynamics in microvascular complications in type 1 diabetes." *Diabetes-Metabolism Research and Reviews* 18(4): 286-304.
Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.
Cense, B., N. Nassif, et al. (2004). "Ultrahigh-Resolution High-Speed Retinal Imaging Using Spectral-Domain Optical Coherence Tomography." *Optics Express* 12(11): 2435-2447.
Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.
Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.
Chartier, T., A. Hideur, et al. (2001). "Measurement of the elliptical birefringence of single-mode optical fibers." *Applied Optics* 40(30): 5343-5353.
Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al. (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of Selected Topics in Quantum Electronics* 5(4): 1134-1142.
Cheong, W. F., S. A. Prahl, et al. (1990). "A Review of the Optical-Properties of Biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.
Choma, M. A., M. V. Sarunic, et al. (2003). "Sensitivity advantage of swept source and Fourier domain optical coherence tomography." *Optics Express* 11(18): 2183-2189.
Choma, M. A., C. H. Yang, et al. (2003). "Instantaneous quadrature low-coherence interferometry with 3×3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 108 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.

(56) References Cited

OTHER PUBLICATIONS

Cioffi, G. A. (2001). "Three common assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama—Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.
Dave, D. P. and T. E. Milner (2000). "Doppler-angle measurement in highly scattering media." *Optics Letters* 25(20): 1523-1525.
de Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.
de Boer, J. F., C. E. Saxer, et al. (2001). "Stable carrier generation and phase-resolved digital data processing in optical coherence tomography." *Applied Optics* 40(31): 5787-5790.
Degroot, P. and L. Deck ( 1993). "3-Dimensional Imaging by Sub-Nyquist Sampling of White-Light Interferograms." *Optics Letters* 18(17): 1462-1464.
Denk, W., J. H. Strickler, et al. (1990). "2-Photon Laser Scanning Fluorescence Microscopy." *Science* 248(4951): 73-76.
Descour, M. R., A. H. O. Karkkainen, et al. (2002). "Toward the development of miniaturized Imaging systems for detection of pre-cancer." *Ieee Journal of Quantum Electronics* 38(2): 122-130.
Dettwiller, L. (1997). "Polarization state interference: A general investigation." *Pure and Applied Optics* 6(1): 41-53.
DiCarlo, C. D., W. P. Roach, et al. (1999). "Comparison of optical coherence tomography imaging of cataracts with histopathology." *Journal of Biomedical Optics* 4.
Ding, Z., Y. Zhao, et al. (2002). "Real-time phase-resolved optical coherence tomography and optical Doppler tomography." *Optics Express* 10(5): 236-245.
Dobrin, P. B. (1996). "Effect of histologic preparation on the cross-sectional area of arterial rings." *Journal of Surgical Research* 61(2): 413-5.
Donohue, D. J., B. J. Stoyanov, et al. (1995). "Numerical Modeling of the Corneas Lamellar Structure and Birefringence Properties." *Journal of the Optical Society of America a—Optics Image Science and Vision* 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.
Drexler, W., A. Baumgartner, et al. (1997). "Submicrometer precision biometry of the anterior segment of the human eye." *Investigative Ophthalmology & Visual Science* 38(7): 1304-1313.
Drexler, W., A. Baumgartner, et al. (1998). "Dual beam optical coherence tomography: signal identification for ophthalmologic diagnosis." *Journal of Biomedical Optics* 3 (1): 55-65.
Drexler, W., O. Findl, et al. (1998). "Partial coherence interferometry: A novel approach to biometry in cataract surgery." *American Journal of Ophthalmology* 126(4): 524-534.
Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.
Drexler, W., C. K. Hitzenberger, et al. (1995). "Measurement of the Thickness of Fundus Layers by Partial Coherence Tomography." *Optical Engineering* 34(3): 701-710.
Drexler, W., U. Morgner, et al. (2001). "Ultrahigh-resolution ophthalmic optical coherence tomography." *Nature Medicine* 7(4): 502-507.
Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.
Drexler, W., H. Sattmann, et al. (2003). "Enhanced visualization of macular pathology with the use of ultrahigh-resolution optical coherence tomography." *Archives of Ophthalmology* 121(5): 695-706.
Drexler, W., D. Stamper, et al. (2001). "Correlation of collagen organization with polarization sensitive imaging of in vitro cartilage: implications for osteoarthritis." *Journal of Rheumatology* 28(6): 1311-8.
Droog, E. J., W. Steenbergen, et al. (2001). "Measurement of depth of burns by laser Doppler perfusion imaging." *Burns* 27(6):561-8.
Dubois, A., K. Grieve, et al. (2004). "Ultrahigh-resolution full-field optical coherence tomography." *Applied Optics* 43(14): 2874-2883.
Dubois, A., L. Vabre, et al. (2002). "High-resolution full-field optical coherence tomography with a Linnik microscope." *Applied Optics* 41(4): 805-812.
Ducros, M., M. Laubscher, et al. (2002). "Parallel optical coherence tomography in scattering samples using a two-dimensional smart-pixel detector array." *Optics Communications* 202(1-3): 29-35.
Ducros, M. G., J. D. Marsack, et al. (2001). "Primate retina imaging with polarization-sensitive optical coherence tomography." *Journal of the Optical Society of America a—Optics Image Science and Vision* 18(12): 2945-2956.
Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.
Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.
Eisenbeiss, W., J. Marotz, et al. (1999). "Reflection-optical multispectral imaging method for objective determination of burn depth." *Burns* 25(8): 697-704.
Elbaum, M., M. King, et al. (1972). "Wavelength-Diversity Technique for Reduction of Speckle Size." *Journal of the Optical Society of America* 62(5): 732-&.
Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

(56) References Cited

OTHER PUBLICATIONS

Essenpreis, M., C. E. Elwell, et al. (1993). "Spectral Dependence of Temporal Point Spread Functions in Human Tissues." *Applied Optics* 32(4): 418-425.
Eun, H. C. (1995). "Evaluation of skin blood flow by laser Doppler flowmetry. [Review] [151 refs]." *Clinics in Dermatology* 13(4): 337-47.
Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.
Feldchtein, F. I., G. V. Gelikonov, et al. (1998). "In vivo OCT imaging of hard and soft tissue of the oral cavity." *Optics Express* 3(6): 239-250.
Feldchtein, F. I., G. V. Gelikonov, et al. (1998). "Endoscopic applications of optical coherence tomography." *Optics Express* 3(6): 257-270.
Fercher, A. F., W. Drexler, et al. (1997). "Optical ocular tomography." *Neuro-Ophthalmology* 18(2): 39-49.
Fercher, A. F., W. Drexler, et al. (1994). *Measurement of optical distances by optical spectrum modulation*. Proceedings of SPIE—The International Society for Optical Engineering.
Fercher, A. F., W. Drexler, et al. (2003). "Optical coherence tomography—principles and applications." *Reports on Progress in Physics* 66(2): 239-303.
Fercher, A. F., C. Hitzenberger, et al. (1991). "Measurement of Intraocular Optical Distances Using Partially Coherent Laser-Light." *Journal of Modern Optics* 38(7): 1327-1333.
Fercher, A. F., C. K. Hitzenberger, et al. (1996). *Ocular partial coherence interferometry*. Proceedings of SPIE—The International Society for Optical Engineering.
Fercher, A. F., C. K. Hitzenberger, et al. (1993). "In-Vivo Optical Coherence Tomography." *American Journal of Ophthalmology* 116(1): 113-115.
Fercher, A. F., C. K. Hitzenberger, et al. (1994). *In-vivo dual-beam optical coherence tomography*. Proceedings of SPIE—The International Society for Optical Engineering.
Fercher, A. F., C. K. Hitzenberger, et al. (1995). "Measurement of Intraocular Distances by Backscattering Spectral Interferometry." *Optics Communications* 117(1-2): 43-48.
Fercher, A. F., C. K. Hitzenberger, et al. (2000). "A thermal light source technique for optical coherence tomography." *Optics Communications* 185(1-3): 57-64.
Fercher, A. F., C. K. Hitzenberger, et al. (2001). "Numerical dispersion compensation for Partial Coherence Interferometry and Optical Coherence Tomography." *Optics Express* 9(12): 610-615.
Fercher, A. F., C. K. Hitzenberger, et al. (2002). "Dispersion compensation for optical coherence tomography depth-scan signals by a numerical technique." *Optics Communications* 204(1-6): 67-74.
Fercher, A. F., H. C. Li, et al. (1993). "Slit Lamp Laser-Doppler Interferometer." *Lasers in Surgery and Medicine* 13(4): 447-452.
Fercher, A. F., K. Mengedoht, et at. (1988). "Eye-Length Measurement by Interferometry with Partially Coherent-Light." *Optics Letters* 13(3): 186-188.
Ferro, P., M. Haelterman, et al. (1991). "All-Optical Polarization Switch with Long Low-Birefringence Fiber." *Electronics Letters* 27(16): 1407-1408.
Fetterman, M. R., D. Goswami, et al. (1998). "Ultrafast pulse shaping: amplification and characterization." *Optics Express* 3(10): 366-375.
Findl, O., W. Drexler, et al. (2001). "Improved prediction of intraocular lens power using partial coherence interferometry." *Journal of Cataract and Refractive Surgery* 27 (6): 861-867.
Fork, R. L., C. H. B. Cruz, et al. (1987). "Compression of Optical Pulses to 6 Femtoseconds by Using Cubic Phase Compensation." *Optics Letters* 12(7): 483-485.
Foschini, G. J. and C. D. Poole (1991). "Statistical-Theory of Polarization Dispersion in Single-Mode Fibers." *Journal of Lightwave Technology* 9(11): 1439-1456.
Francia, C., F. Bruyere, et al. (1998). "PMD second-order effects on pulse propagation in single-mode optical fibers." *Ieee Photonics Technology Letters* 10(12): 1739-1741.
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto, J. G., M. E. Brezinski, et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Optical Engineering* 20(1): 25-30.
Galtarossa, A., L. Palmieri, et al. (2000). "Statistical characterization of fiber random birefringence." *Optics Letters* 25(18): 1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikonov, V. M., G. V. Gelikonov, et al. (1995). "Coherent Optical Tomography of Microscopic Inhomogeneities in Biological Tissues." *Jetp Letters* 61(2): 158-162.
George, N. and A. Jain (1973). "Speckle Reduction Using Multiple Tones of Illumination." *Applied Optics* 12(6): 1202-1212.
Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a—Optics Image Science and Vision* 17(2): 328-334.
Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonace imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.
Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

(56) References Cited

OTHER PUBLICATIONS

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmology* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in volume scatterers with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interferometric Ellipsometry and Precision Reflectometry." *Journal of Physics E-Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Topography of diabetic macular edema with optical coherence tomography." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Welle (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vivo, ultrahigh-resolution optical coherence tomography." *Optics Letters* 29(19): 2261-2263.
Hirakawa, H., H. Iijima, et al. (1999). "Optical coherence tomography of cystoid macular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.
Hitzenberger, C. K., A. Baumgartner, et al. (1999). "Dispersion effects in partial coherence interferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154 (4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., a. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Hotate, K. and T. Okugawa (1994). "Optical Information-Processing by Synthesis of the Coherence Function." *Journal of Lightwave Technology* 12(7): 1247-1255.
Hourdakis, C. J. and A. Perris (1995). "A Monte-Carlo Estimation of Tissue Optical-Properties for Use in Laser Dosimetry." *Physics in Medicine and Biology* 40(3): 351-364.

(56) References Cited

OTHER PUBLICATIONS

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a—Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.

R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.

W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.

J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.

D.J. Bowery et al., (1999) "Patterns of Gastritis in Patients with Gastro-Oesophageal Reflux Disease,", Gut, vol. 45, pp. 798-803.

O'Reich et al., (2000) "Expression of Oestrogen and Progesterone Receptors in Low-Grade Endometrial Stromal Sarcomas,", British Journal of Cancer, vol. 82, No. 5, pp. 1030-1034.

M.I. Canto et al., (1999) "Vital Staining and Barrett's Esophagus," Gastrointestinal Endoscopy, vol. 49, No. 3, Part 2, pp. S12-S16.

S. Jackie et al., (2000) "In Vivo Endoscopic Optical Coherence Tomography of the Human Gastrointestinal Tract-Toward Optical Biopsy," Encoscopy, vol. 32, No. 10, pp. 743-749 .

(56) References Cited

OTHER PUBLICATIONS

E. Montgomery et al.,"Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia -Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 µm Communications Window," Electronics Letters, vol. 27, pp. 95-96.
Office Action dated Jan. 25, 2010 for U.S. Appl. No. 11/537,048.
International Search Report dated Jan. 27,2 010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interfece Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al. "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.

Wojtkowski, Macie Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy", Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
International Search Report and Written Opinion dated Feb. 23, 2011 for PCT/US2010/041923.
Extended European Search Report dated Dec. 14, 2010 for EP 10182301.1.
International Search report dated Apr. 29, 2011 for PCT/US2010/051715.
International Search report dated Sep. 13, 2010 for PCT/US2010/023215.
International Search report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illuminatlon microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647:125 (1992).
A.A. Bednov et al., "Investigation of Statistical Properties of Lymph Flow Dynamics Using Speckle-Microscopy," SPIE, 2981: 181-90 (1997).
Feng et al., "Mesoscopic Conductors and Correlations in Laser Speckle Patterns" Science, New Series, vol. 251, No. 4994, pp. 633-639 (Feb. 8, 1991).

(56) References Cited

OTHER PUBLICATIONS

Lee et al., "The Unstable Atheroma," Arteriosclerosis, Thrombosis & Vascular Blology, 17:1859-67 (1997).
Japanese language Appeal Decicion dated Jan. 10, 2012 for JP 2006-503161.
Notice of Reasons for Rejection dated Nov. 2, 2011 for JP 2008-509233.
Notice of Reasons for Rejection dated Nov. 21, 2011 for JP 2007-525075.
Extended European Search Report dated Nov. 28, 2011 for EP 09767845.2.
International Search Report and Written Opinion for PCT/US2011/037916 dated Dec. 27, 2011.
International Search Report and Written Opinion for PCT/US2011/039066 dated Dec. 28, 2011.
Communication pursuant to Article 94(3) for EP 10186189.6 dated Dec. 22, 2011.
International Search Report and Written Opinion for PCT/US2011/038421 dated Jan. 12, 2012.
Japanese Language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP2003516531.
International Search Report and Written Opinion dated Feb. 9, 2012 based on PCT/US2011/034810.
European Search Report dated Mar. 2, 2012 for EP 11188120.7.
Japanese Notice of Reasons for Rejection dated Feb. 17, 2012 for JP 2007-539336.
Japanese Notice of Reasons for Rejection dated Feb. 15, 2012 for JP 2008-553509.
Japanese Notice of Reasons for Rejection dated Mar. 27, 2012 for JP 2008-554495.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese Notice of Reasons for Rejection dated Dec. 12, 2011 for JP 2008-533712.
Japanese Notice of Reasons for Rejection dated Mar. 27, 2012 for JP 2003-102672.
Jopson, R. MThe ., L. E. Nelson, et al. (1999). "Measurement of second-order polarization-mode dispersion vectors in optical fibers." Ieee Photonics Technology Letters 11 (9): 1153-1155.
Jost, B. M., A. V. Sergienko, et al. (1998). "Spatial correlations of spontaneously down-converted photon pairs detected with a single-photon-sensitive CCD camera." Optics Express 3(2): 81-88.
Kaplan, B., E. Compain, et al. (2000). "Phase-modulated Mueller ellipsometry characterization of scattering by latex sphere suspensions." Applied Optics 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." Archives of Ophthalmology 120(6): 701-13; discussion 829-30.
Kasuga, Y., J. Arai, et al. (2000). "Optical coherence tomograghy to confirm early closure of macular holes." American Journal of Ophthalmology 130(5): 675-6.
Kaufman, T., S. N. Lusthaus, et al. (1990). "Deep Partial Skin Thickness Burns—a Reproducible Animal-Model to Study Burn Wound-Healing." Burns 16(1): 13-16.

Kemp, N. J., J. Park, et al. (2005). "High-sensitivity determination of birefringence in turbid media with enhanced polarization-sensitive optical coherence tomography." Journal of the Optical Society of America a—Optics Image Science and Vision 22(3): 552-560.
Kerrigan-Baumrind, L. A., H. A. Quigley, et al. (2000). "Number of ganglion cells in glaucoma eyes compared with threshold visual field tests in the same persons." Investigative Ophthalmology & Visual Science 41(3): 741-8.
Kesen, M. R., G. L. Spaeth, et al. (2002). "The Heidelberg Retina Tomograph vs clinical impression in the diagnosis of glaucoma." American Journal of Ophthalmology 133(5): 613-6.
Kienle, A. and R. Hibst (1995). "A New Optimal Wavelength for Treatment of Port-Wine Stains." Physics in Medicine and Biology 40(10): 1559-1576.
Kienle, A., L. Lilge, et al. (1996). "Spatially resolved absolute diffuse reflectance measurements for noninvasive determination of the optical scattering and absorption coefficients of biological tissue." Applied Optics 35(13): 2304-2314.
Kim, B. Y. and S. S. Choi (1981). "Analysis and Measurement of Birefringence in Single-Mode Fibers Using the Backscattering Method." Optics Letters 6(11): 578-580.
Kimel, S., L. O. Svaasand, et al. (1994). "Differential Vascular-Response to Laser Photothermolysis." Journal of Investigative Dermatology 103(5): 693-700.
Kloppenberg, F. W. H., G. Beerthuizen, et al. (2001). "Perfusion of burn wounds assessed by Laser Doppler Imaging is related to burn depth and healing time." Burns 27(4): 359-363.
Knighton, R. W. and X. R. Huang (2002). "Analytical methods for scanning laser polarimetry." Optics Express 10(21): 1179-1189.
Knighton, R. W., X. R. Huang, et al. (2002). "Analytical model of scanning laser polarimetry for retinal nerve fiber layer assessment." Investigative Ophthalmology & Visual Science 43(2): 383-392.
Knuettel, A. R. S., Joseph M.: Shay, M.; Knutson, Jay R. (1994). "Stationary low-coherence light imaging and spectroscopy using a CCD camera." Proc. SPIE , vol. 2135: p. 239-250.
Knuttel, A. and M. Boehlau-Godau (2000). "Spatially confined and temporally resolved refractive index and scattering evaluation in human skin performed with optical coherence tomography." Journal of Biomedical Optics 5(1): 83-92.
Knuttel, A. and J. M. Schmitt (1993). "Stationary Depth-Profiling Reflectometer Based on Low-Coherence Interferometry." Optics Communications 102(3-4): 193-198.
Knuttel, A., J. M. Schmitt, et al. (1994). "Low-Coherence Reflectometry for Stationary Lateral and Depth Profiling with Acoustooptic Deflectors and a Ccd Camera." Optics Letters 19(4): 302-304.
Kobayashi, M., H. Hanafusa, et al. (1991). "Polarization-Independent Interferometric Optical-Time-Domain Reflectometer." Journal of Lightwave Technology 9(5): 623-628.
Kolios, M. C., M. D. Sherar, et al. (1995). "Large Blood-Vessel Cooling in Heated Tissues—a Numerical Study." Physics in Medicine and Biology 40(4): 477-494.
Koozekanani, D., K. Boyer, et al. (2001). "Retinal thickness measurements from optical coherence tomography using a Markov boundary model." Ieee Transactions on Medical Imaging 20(9): 900-916.
Kop, R. H. J. and R. Sprik (1995). "Phase-sensitive interferometry with ultrashort optical pulses." Review of Scientific Instruments 66(12): 5459-5463.
Kramer, R. Z., J. Bella, et al. (1999). "Sequence dependent conformational variations of collagen triple-helical structure." Nature Structural Biology 6(5): 454-7.
Kulkami, M. D., T. G. van Leeuwen, et al. (1998). "Velocity-estimation accuracy and frame-rate limitations in color Doppler optical coherence tomography." Optics Letters 23(13): 1057-1059.
Kwon, Y. H., C. S. Kim, et al. (2001). "Rate of visual field loss and long-term visual outcome in primary open-angle glaucoma." American Journal of Ophthalmology 132(1): 47-56.
Kwong, K. F., D. Yankelevich, et al. (1993). "400-Hz Mechanical Scanning Optical Delay-Line." Optics Letters 18(7): 558-560.

(56) References Cited

OTHER PUBLICATIONS

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life.* 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Ouantum Electronics* 23(1): 59-64.

Martinez, O. E., J. P. Gordon, et al. (1984). "Negative Group-Velocity Dispersion Using Refraction." *Journal of the Optical Society of America a—Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a—Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics Part 1—Regular Papers Short Notes & Review Papers* 38(5A): 2978-2982.

(56) References Cited

OTHER PUBLICATIONS

Molteno, A. C., N. J. Bosma, et al. (1999). "Otago glaucoma surgery outcome study: long-term results of trabeculectomy—1976 to 1995." *Ophthalmology* 106(9): 1742-50.
Morgner, U., W. Drexler, et al. (2000). "Spectroscopic optical coherence tomography." *Optics Letters* 25(2): 111-113.
Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.
Mourant, J. R., A. H. Hielscher, et al. (1998). "Evidence of intrinsic differences in the light scattering properties of tumorigenic and nontumorigenic cells." *Cancer Cytopathology* 84(6): 366-374.
Muller, M., J. Squier, et al. (1998). "Dispersion pre-compensation of 15 femtosecond optical pulses for high-numerical-aperture objectives." *Journal of Microscopy—Oxford* 191: 141-150.
Muscat, S., N. McKay, et al. (2002). "Repeatability and reproducibility of corneal thickness measurements by optical coherence tomography." *Investigative Ophthalmology & Visual Science* 43(6): 1791-5.
Musch, D. C., P. R. Lichter, et al. (1999). "The Collaborative Initial Glaucoma Treatment Study. Study Design, MethodsR, and Baseline Characteristics of Enrolled Patients." *Ophthalmology* 106: 653-662.
Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.
Nelson, J. S., K. M. Kelly, et al. (2001). "Imaging blood flow in human port-wine stain in situ and in real time using optical Doppler tomography." *Archives of Dermatology* 137(6): 741-744.
Newson, T. P., F. Farahi, et al. (1988). "Combined Interferometric and Polarimetric Fiber Optic Temperature Sensor with a Short Coherence Length Source." *Optics Communications* 68(3): 161-165.
Nov., L. J. (1993). "Recovery of the Matrix Operators in the Similarity and Congruency Transformations—Applications in Polarimetry." *Journal of the Optical Society of America a—Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678-680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multi-functional spectral-domain optical coherence tomography at 1.3 mu m." *Optics Express* 13(11): 3931-3944.
Park, D. H., J. W. Hwang, et al. (1998). "Use of laser Doppler flowmetry for estimation of the depth of burns." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and a confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.
Podoleanu, A. G., M. Seeger, et al. (1998). "Transversal and longitudinal images from the retina of the living eye using low coherence reflectometry." *Journal of Biomedical Optics* 3(1): 12-20.
Poole, C. D. (1988). "Statistical Treatment of Polarization Dispersion in Single -Mode Fiber." *Optics Letters* 13(8): 687-689.
Povazay, B., K. Bizheva, et al. (2002). "Submicrometer axial resolution optical coherence tomography." *Optics Letters* 27(20): 1800-1802.
Qi, B., A. P. Rimmer, et al. (2004). "Dynamic focus control in high-speed optical coherence tomography based on a microelectromechanical mirror." *Optics Communications* 232(1-6): 123-128.
Radhakrishnan, S., a. M. Rollins, et al. (2001). "Real-time optical coherence tomography of the anterior segment at 1310 nm." *Archives of Ophthalmology* 119(8): 1179-1185.
Rogers, A. J. (1981). "Polarization-Optical Time Domain Reflectometry—a Technique for the Measurement of Field Distributions." Applied Optics 20(6): 1060-1074.
Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rollins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phanto, ehms containing densely packed scatterers." *Optics Letters* 25(4): 239-241.
Sarunic, M. V., M. A. Choma, et al. (2005). "Instantaneous complex conjugate resolved spectral fiber domain and swept-source OCT using 3x3 couplers." *Optics Express* 13(3): 957-967.
Sathyam, U. S., B. W. Colston, et al. (1999). "Evaluation of optical coherence quantitation of analytes in turbid media by use of two wavelengths." *Applied Optics* 38(10): 2097-2104.
Schmitt, J. M. (1997). "Array detection for speckle reduction in optical coherence microscopy." *Physics in Medicine and Biology* 42(7): 1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a—Optics Image Science and Vision* 14(6): 1231-1242.
Schmitt, J. M., S. L. Lee, et al. (1997). "An optical coherence microscope with enhanced resolving power in thick tissue." *Optics Communications* 142(4-6): 203-207.

(56) References Cited

OTHER PUBLICATIONS

Schmitt, J. M., S. H. Xiang, et al. (1998). "Differential absorption imaging with optical coherence tomography." *Journal of the Optical Society of America a—Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy."

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optical catheter-endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a—Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

(56) References Cited

OTHER PUBLICATIONS

Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.
Yabushita, H. B., B.E., Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."
Yang, C., A. Wax, et al. (2001). "Phase-dispersion optical tomography." *Optics Letters* 26(10): 686-688.
Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." *Optics Communications* 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13) : 424-431.
Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Ophthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23): 5614-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.

(56) References Cited

OTHER PUBLICATIONS

Boas et al., "Diffusing temporal light correlation for burn diagnosis", *SPIE*, 1999, 2979:468-477.
David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.
Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.*, 1997, 14(9):2269-2277.
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23-S 27.
T. Yoshimura et al., "Statistical properties of dynamic speckles", *J. Opt. Soc. Am A.* 1986, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using FT-IR microspectroscopy", *Atherosclerosis*, May 1993, 181-1930.
N.V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", *Phys. Med. Biol.* 2000 (45): 1495-1509.
S.B. Adams Jr. et al., "The use of polarization sensitive optical coherence tomography and elastography to assess connective tissue", Optical Soc. of American Washington 2002, p. 3.
International Search Report for International Patent application No. PCT/US2005/039740.

International Written Opinion for International Patent application No. PCT/US2005/039740.
International Search Report for International Patent application No. PCT/US2005/030294.
International Written Opinion for International Patent application No. PCT/US2005/043951.
International Search Report for International Patent application No. PCT/US2005/043951.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664.
International Written Opinion for International Patent application No. PCT/US2005/023664.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704.
International Search Report for International Patent application No. PCT/US2004/039454.
International Written Opinion for International Patent application No. PCT/US2004/039454.
PCT International Preliminary Report on Patentability for International Application No. PCT/US2004/038404 dated Jun. 2, 2006.
Notice of Reasons for Rejection and English translation for Japanese Patent Application No. 2002-538830.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.

(56) References Cited

OTHER PUBLICATIONS

Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers E.J et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" *Gastrointestinal Endoscopy* vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.
Poneros, John M. et al. (2001) "Diagnosis of Specialized Intestinal Metaplasia by Optical Coherence Tomography" *Gastroenterology* vol. 120, pp. 7-12.
Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.
Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.
Sampliner, Richard E. (2004) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje et al. (2006) "Performance of the Aer-O-Scope, a Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.
Vogel, Alfred et al. (2003) "Mechanisms of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209.
Anderson, R. Rox et al. (1983) "Selective Photothermolysis" Precise Microsurgery by Selective Absorption of Pulsed Radiation *Science* vol. 220, No. 4596, pp. 524-527.
Jacques, Steven L. (1993) "Role of Tissue Optics and Pulse Duration on Tissue Effects During High-Power Laser Irradiation" *Applied Optics* vol. 32, No. 13, pp. 2447-2454.
Nahen, Kester et al. (1999) "Investigations on Acousstic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optotherrnal Properties of Heated Tissues" *International Journal of Thermophysics* vol. 26., No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry a. et al (2002) "Speckle-Contrast Monitoring of Tissue Thermal Modification" *Applied Optics* vol. 41, No. 28, pp. 5989-5996.
Morelli, J.G., et al (1986) "Tunable Dye Laser (577 nm) Treatment of Port Wine Stains" *Lasers in Surgery and Medicine* vol. 6, pp. 94-99.

(56) References Cited

OTHER PUBLICATIONS

French, P.M.W. et al. (1993) "Continuous-wave Mode-Locked Cr$^{4+}$: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: Al$_2$O$_3$ Laser" *Optics Letters* vol. 19, No. 22, pp. 1858-1860.
Bouma, B et al. (1995) "High Resolution Optical Coherence Tomography Imaging Using a Mode-Locked Ti: Al$_2$O$_3$ Laser Source" *Optics Letters* vol. 20, No. 13, pp. 1486-1488.
Fernández, Cabrera Delia et al. "Automated detection of retinal layer structures on optical coherence tomography images", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19$^{th}$ International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report for Application No. 05791226.3.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.

(56) References Cited

OTHER PUBLICATIONS

PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.

\* cited by examiner

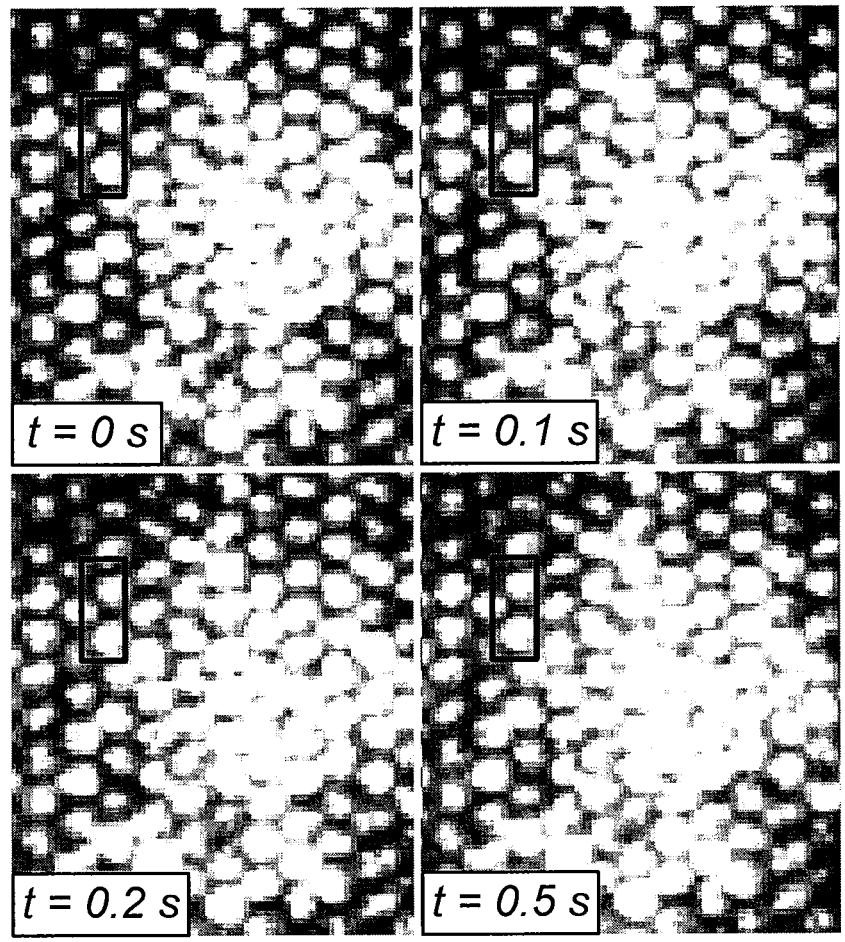
F I G. 5

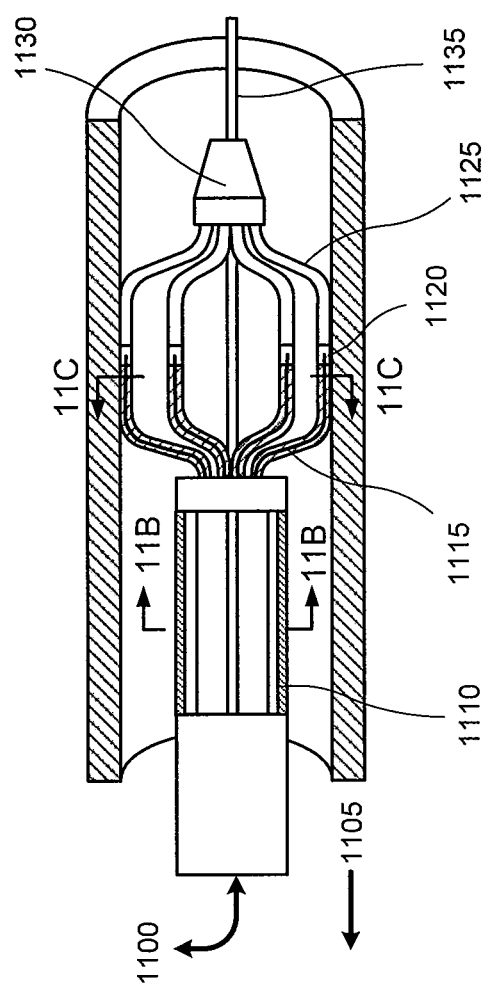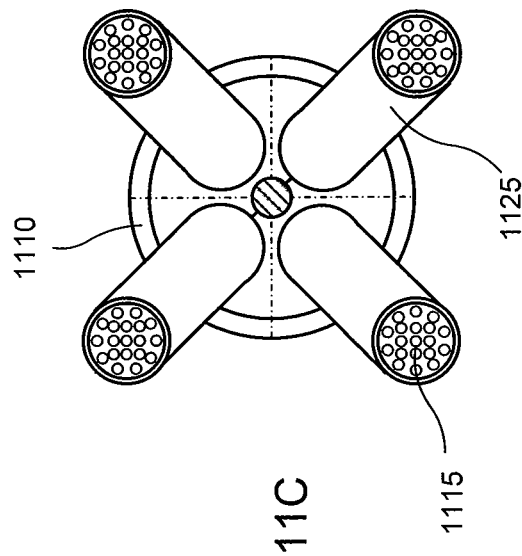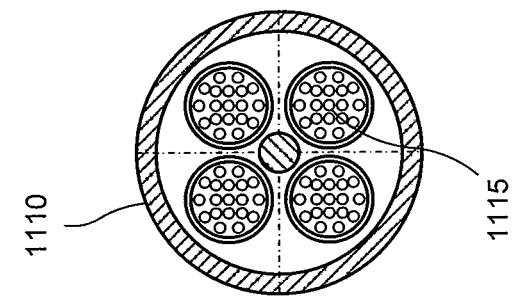
FIG. 11A
FIG. 11B
FIG. 11C

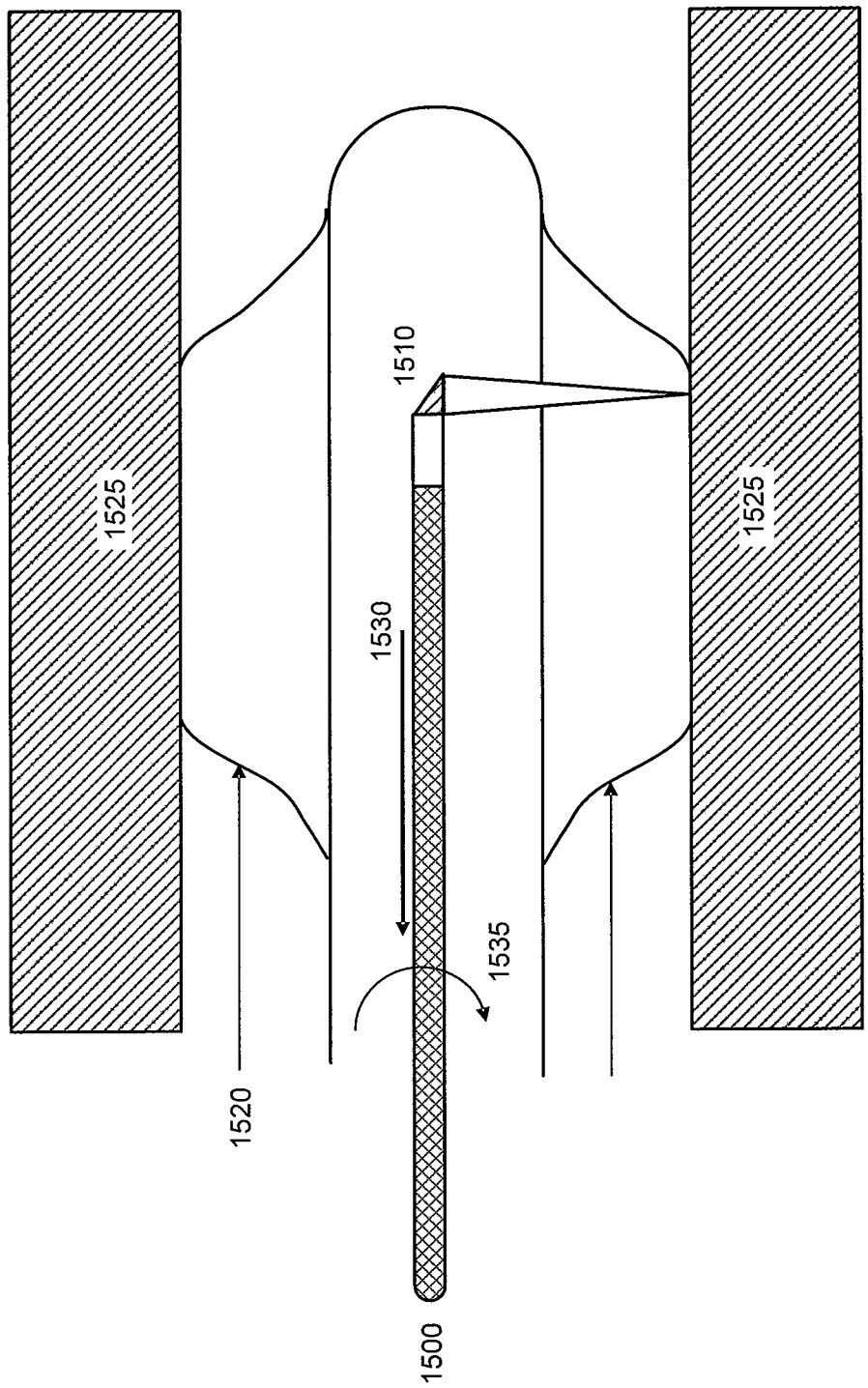
F I G. 15

SYSTEM AND METHOD PROVIDING INTRACORONARY LASER SPECKLE IMAGING FOR THE DETECTION OF VULNERABLE PLAQUE

CROSS-REFERENCE TO RELATED APPLICATION(S)

This application is based upon and claims the benefit of priority from U.S. Patent Application Ser. No. 60/909,288, filed Mar. 30, 2007, the entire disclosure of which are incorporated herein by reference.

FIELD OF THE INVENTION

The present invention relates to imaging at least one portion of a sample, and more particularly to system and method providing intracoronary laser speckle imaging for the detection of vulnerable plaque.

BACKGROUND OF THE INVENTION

Ischemic cardiovascular disease, the leading cause of death in industrialized societies, can be frequently preceded by the rupture of unstable atherosclerotic plaque. The intricate interplay between biomechanical, compositional and morphological factors may influence plaque stability. Certain exemplary techniques that facilitate a composite understanding of the link between these factors can assist in identifying rupture-prone plaques, guiding treatment and for investigating mechanisms associated with plaque stabilization therapies.

Another technique has been investigated, i.e., a Laser Speckle Imaging ("LSI") technique which can provide measurements related to biomechanical, compositional and morphological factors potentially yielding an advantageous technique for detecting high-risk plaques in patients. Laser speckle is a granular pattern formed by the interference of coherent laser light scattered from tissue. The speckle pattern is dynamically modulated by Brownian motion of endogenous particles within tissue, which is governed by the viscoelasticity of tissue. In LSI, the extent of Brownian motion can be quantified by the cross-correlation of speckle images obtained as a function of time. The exemplary techniques of using arterial specimens ex vivo have demonstrated that the index of viscoelasticity measured by LSI can be related to plaque type, structure and composition.

While exemplary prior ex vivo studies can indicate an advantageous diagnostic potential of LSI, important technical challenges may exist in extending LSI technology and techniques for an intracoronary in vivo use. In order to achieve clinical viability, the exemplary intracoronary LSI system and technique can, e.g., (a) facilitate a rapid screening of long coronary segments (e.g., ~5 cm) to identify high-risk plaques, (b) obtain diagnostic information in the presence of coronary blood flow, and (c) retain an adequate motion stability over the cardiac cycle.

Atherosclerotic Plaque:

Despite widespread efforts towards its detection and therapy, thrombus mediated ischemic cardiovascular disease still remains the leading cause of mortality in industrialized societies. The rupture of unstable coronary atherosclerotic plaque frequently precedes a majority of ischemic cardiovascular events. It is believed that a certain type of plaque, termed the necrotic-core fibroatheroma (NCFA) is particularly vulnerable to rupture. Typical characteristics of vulnerable NCFA's include the presence of a thin (<65 μm), mechanically weak fibrous cap, a large compliant necrotic core, and activated macrophages near the fibrous cap.[1,2] It is recognized that a complex liaison between biomechanical, compositional and morphological mechanisms influences plaque stability. These mechanisms can include the proteolysis of fibrous cap collagen by matrix metalloproteinases (MMP) released by activated macrophages and apoptosis of intimal SMC's, which impedes collagen synthesis.[3,4,5] Mediated by endothelial production of nitric oxide, TGF-β, and plasmin, this dynamic imbalance between collagen synthesis and degradation causes a net reduction in collagen content and mechanically weakens the fibrous cap.[6] Systemic statin therapy likely favorably reverses these factors and stabilizes plaques, thereby dramatically reducing the incidence of acute coronary events.[7,8,9,10,11]

Evidence suggesting that biomechanical factors play an important part in determining plaque stability is compelling. Differential shear stresses can induce focal variations in plaque composition, influencing susceptibility to plaque rupture, atherosclerosis progression and coronary thrombosis.[6] Finite element studies have suggested that rupture of the fibrous cap is greatly influenced by regions of high circumferential stress typically in the lateral cap shoulders.[12,13,14] Computational and experimental analyses have demonstrated that local stress distributions are affected by atheroma structure and material properties,[15] and higher differential strain is measured in lipid rich tissue.[16] The accumulation of a compliant lipid pool influences the local stress distributions within the plaque resulting in rupture of the fibrous cap.[2,12] Cyclic mechanical strain within the arterial wall affects macrophage gene expression and SMC proliferation.[17] Histology studies have shown the localization of matrix metalloproteinase-1 (MMP-1) in regions of high circumferential strain within plaques, suggesting that mechanical stress/strain influences MMP release and weakens plaque structure.[18] The exemplary processes leading to plaque vulnerability and the therapeutic mechanisms contributing to plaque stabilization are multi-factorial, and techniques that allow a composite understanding of these factors are invaluable for identifying rupture-prone plaques, guiding treatment and for providing insights regarding mechanisms associated with plaque stabilization therapies.

Detecting Unstable Coronary Plaques: A variety of catheter-based imaging methods such as IVUS, magnetic resonance imaging (MRI), angioscopy, thermography, infrared and Raman spectroscopy, and optical coherence tomography (OCT) have been investigated for identifying unstable plaque.[19,20,21,22,23,24,25,26,27,28,29] These exemplary methods are complementary to techniques that measure biomechanical properties, since they provide important structural and compositional information associated with plaque stability. To address the likely need for evaluating plaque biomechanical properties, IVUS-based elastography has been developed to compute local strain in atherosclerotic plaque in response to intra-luminal pressure differentials exerted on the arterial wall.[16,30] In IVUS elastography, arterial tissue deformation may be estimated using cross-correlation analysis and strains are computed from the tissue velocity gradient. Exemplary approaches utilized for IVUS elastography can be applied to OCT to provide higher spatial resolution of strain estimation and enhanced tissue contrast relative to IVUS.[31] Such exemplary methods for strain imaging using elastography enable the measurement of arterial response to a dynamic external loading environment, providing an indirect evaluation of intrinsic tissue compliance, which depends on tissue viscoelasticity. However, a measurement of plaque viscoelasticity with these approaches may be challenging, generally using a priori knowledge of the microscopic plaque morphology and loading conditions to solve the inverse problem.

Brownian Motion and Viscoelasticity:

The passive dynamics of particles suspended in a viscoelastic material may be potentially of significant utility in evaluating the bulk mechanical properties of the medium. In 1827, Robert Brown observed and noted that small particles suspended in a viscous medium ceaselessly move about following a random path. This effect, termed as Brownian motion, can be caused due to the thermal motion of molecules which incessantly bombard suspended particles within the medium, causing random particular motion. Mason and Weitz demonstrated that the Brownian motion of suspended particles is intimately related to the structure and viscoelastic properties of the suspending medium, and suspended particles exhibit larger range of motions when their local environment is less rigid.[32] Exemplary studies have shown that the viscoelastic modulus of polymer materials can be evaluated by suspending exogenous microspheres and measuring the time scale and mean square displacement of microscopic trajectories using diffuse light scattering techniques.[33] Yamada et al measured the viscoelastic properties of living cells from the Brownian motion of endogenous granules suspended within the cytoskeletal network.[34] By applying these concepts a further optical technique has been investigated, termed Laser Speckle Imaging, which analyzes the intrinsic Brownian motion of endogenous microscopic particles suspended within atherosclerotic plaques to possibly evaluate plaque viscoelasticity.

Laser Speckle Imaging of Atherosclerotic Plaques:

When an object is imaged using highly coherent light from a laser, a granular pattern of multiple bright and dark spots becomes apparent on the image, which bears no perceptible relationship to the macroscopic structure of the object, as shown in FIG. 1. These random intensity patterns, known as laser speckle,[35] can occur in two situations, e.g., (i) when coherent light is reflected from a surface which is rough on the scale of an optical wavelength, and (ii) when coherent light propagates through and is scattered by a medium with random refractive index fluctuations such as in tissue.

The interference of light returning from the random surface or medium generally causes laser speckle. Laser speckle formed from scattering within tissue is exquisitely sensitive to Brownian motion. The Brownian motion of endogenous light scattering particles in tissue may cause scatterer locations and optical path lengths to dynamically change resulting in time dependent intensity modulations of laser speckle. The rate of laser speckle modulation is dependent on the extent of motion of suspended scatterers, which is in turn influenced by viscoelasticity of the medium. Consequently, in a NCFA, due to the relatively low viscosity of lipid, endogenous scatterers within the compliant necrotic core exhibit more rapid Brownian motion compared to the stiffer fibrous regions of the plaque.

Since scatterer motion can govern the modulation of laser speckle, the measurement of temporal intensity variations of laser speckle patterns provides information about the viscoelastic properties of the plaque. Using these principles, it has been successfully demonstrated that the measurement of intensity modulations of time-varying laser speckle patterns provides a highly sensitive technique for evaluating atherosclerotic plaques.[36]

While the measurement of composite plaque stability metrics using LSI is invaluable, the opportunity to obtain these measurements is gated by the feasibility of conducting LSI in the coronary vasculature in vivo. Key technical challenges exist in developing an intracoronary LSI device that allows rapid imaging of long coronary segments in the presence of blood flow, while retaining adequate motion stability over the cardiac cycle.

Accordingly, there may be a need to overcome at least some of the deficiencies described herein above.

OBJECTS AND SUMMARY OF EXEMPLARY EMBODIMENTS

To address and/or overcome the above-described problems and/or deficiencies as well as other deficiencies, exemplary systems and methods can be provided for providing intracoronary laser speckle imaging for a detection of vulnerable plaque. Such deficiencies can be addressed using the exemplary embodiments of the present invention.

In one exemplary embodiment of the present invention, an apparatus and method can be provided, for analyzing tissue. For example, the apparatus can include at least one first arrangement configured to illuminate at least one anatomical structure with at least one of at least one electromagnetic radiation. The apparatus can also include at least one second arrangement that may include at least two wave-guiding arrangements associated with one another that are configured to receive a further electro-magnetic radiation reflected from the tissue and transmit at least one speckle pattern associated with the further electro-magnetic radiation. The wave-guiding arrangements may be structured so as to reduce crosstalk there between.

According to another exemplary embodiment, the wave-guiding arrangements can include at least two fibers which can be provided in a fiber bundle. The first arrangement may include at least one section of at least one of the wave-guiding arrangements. The first arrangement can also include at least two wave-guiding further arrangements and/or a further single fiber. The wave-guiding arrangements may be separated from one another by a predetermined distance which can be selected so as to reduce the crosstalk. The wave-guiding arrangements may include respective cores, and the predetermined distance can be approximately at least 3 times a width of at least one of the cores.

According to yet another exemplary embodiment of the present invention, at least one section of at least one of the wave-guiding arrangements can be covered by a cladding material which has characteristics so as to reduce the crosstalk. The wave-guiding arrangements may be provided in a leached fiber bundle. Further, at least one of the wave-guiding arrangements can include a wave-guide region that has an angle for transceiving the electro-magnetic radiation that has at least one characteristic so as to reduce the crosstalk.

In still another exemplary embodiment of the present invention, the first arrangement can include a plurality of first arrangements, and the second arrangement may include a plurality of second arrangements. At least one third arrangement can be provided which may be configured to move the first arrangement and/or the second arrangement. The first arrangement and/or the second arrangement can be structured to be provided in a particular proximity to an anatomical structure (e.g., a blood vessel). At least one fourth arrangement may be provided that can be structured to (i) partially occlude the blood vessel, and/or (ii) flush a fluid from or within the blood vessel. The second arrangement may transmit at least one angioscopy image.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 5 are exemplary laser speckle images static Teflon obtained using a low cross talk optical fiber bundle according to an exemplary embodiment of the present invention;

FIG. 11A is a side view of a diagram of an intracoronary LSI catheter arrangement according to an exemplary embodiment of the present invention;

FIG. 11B is a front cut-away view of a schematic diagram of the cross-sectional view of the exemplary embodiment shown in FIG. 11A at a particular exemplary location;

FIG. 11C is a rear cut-away view of a schematic diagram of the cross-sectional view of the exemplary embodiment shown in FIG. 11A at another particular exemplary location;

FIG. 15 a side view of the intracoronary LSI catheter arrangement according to yet another exemplary embodiment of the present invention;

Figure 1:
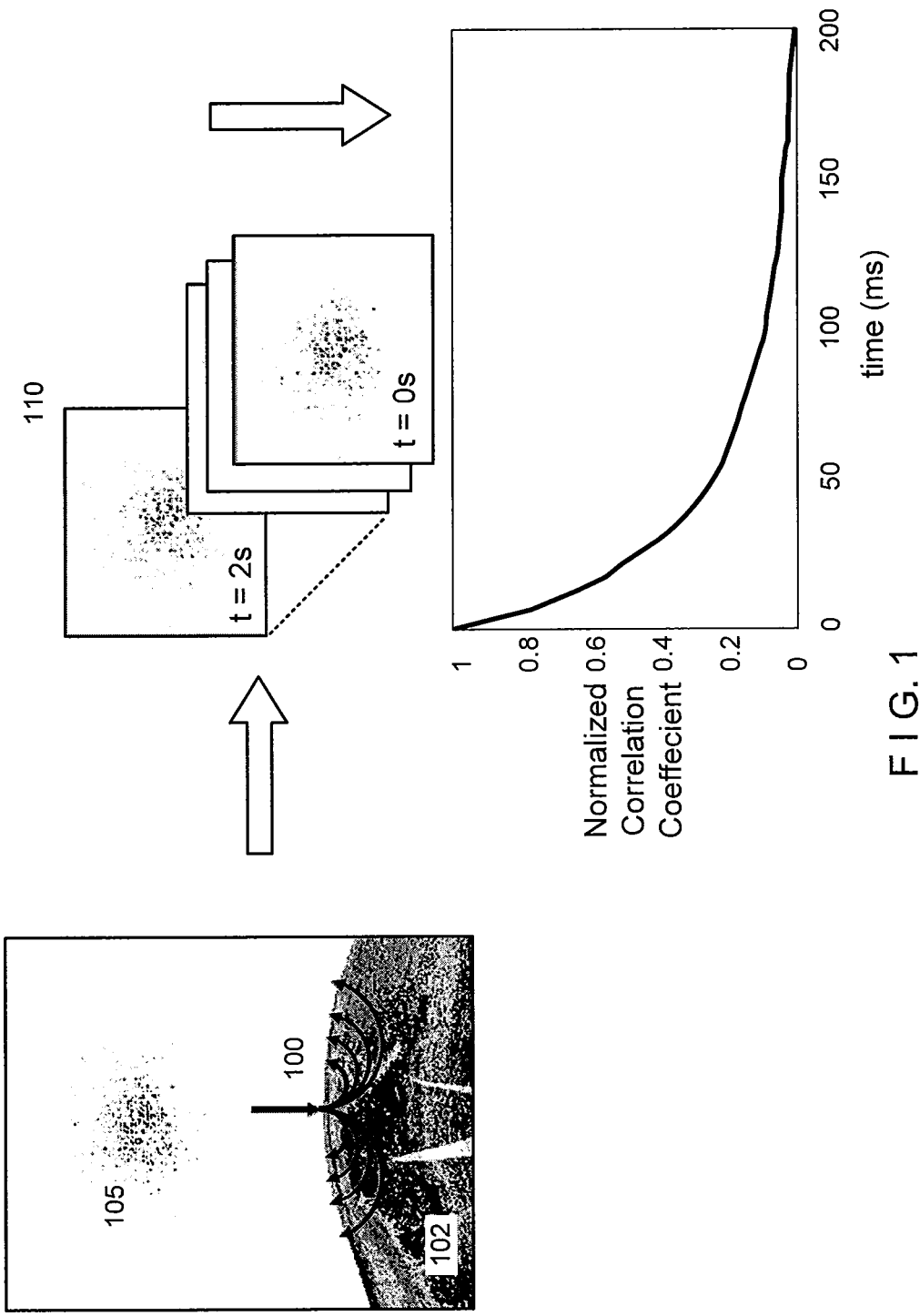
FIG. 1 are illustration of various exemplary results of Laser Speckle Imaging ("LSI") according to an exemplary embodiment of the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

Figure 2:
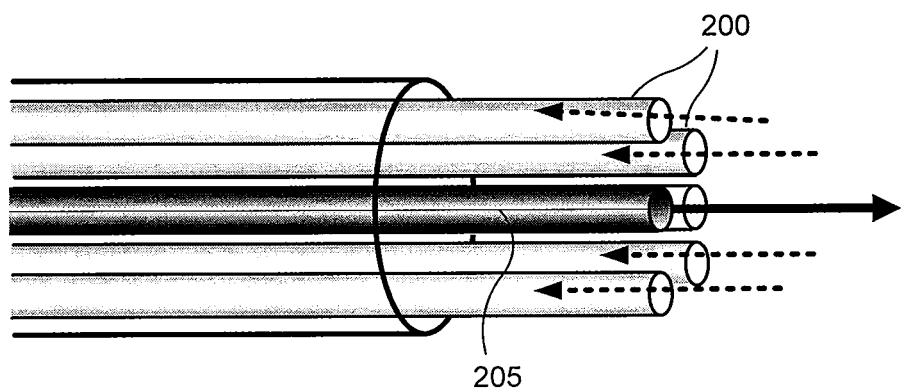
FIG. 2 is perspective side view of a schematic diagram of a wave-guiding arrangement for performing intravascular LSI according to an exemplary embodiment of the present invention.

A study, (published in Circulation[37]), has been performed to demonstrate the capability of LSI for differentiating atherosclerotic plaque type, and for assessing plaque morphology and composition. For example, 118 aortic specimens obtained from 14 human cadavers have been analyzed using LSI. Light (e.g., 632 nm) from a Helium-Neon laser (shown in FIG. 1) 100 was focused on the luminal surface of the artery 102 and a CCD camera (TM-6710CL, Pulnix, Sunnyvale, Calif.) captured laser speckle images 105 at 240 frames/s for 2 seconds (see FIG. 1). As shown in FIG. 2, time-varying laser speckle images 110 were analyzed using normalized two-dimensional cross-correlation techniques 38 to determine the speckle decorrelation time constant, $\tau$, which is inversely dependent on the rate of change of the speckle image 115. The time constant, $\tau$, was computed by exponential fitting of the normalized speckle decorrelation data 115.

These prior studies that have demonstrated the diagnostic potential of LSI for detecting high-risk plaques have been conducted ex vivo. In order to conduct intracoronary LSI in vivo, the laser speckle pattern should be transmitted from the coronary wall to the image detector. As shown in FIG. 2, small-diameter, flexible exemplary optical fiber bundles 200, 205, e.g., which can be similar to those used in coronary angioscopy,[6] may be incorporated into an intravascular catheter for this purpose. However, the capability of fiber bundles to reliably transmit laser speckle data in the presence of motion such as that encountered in coronary arteries has not been evaluated.

Exemplary Implementation of Optical Fiber Bundles for LSI

According to one exemplary embodiment of the present invention, it is possible to provide LSI through optical fiber bundles in the presence cardiac motion.

To that end, exemplary LSI procedures can be performed on thoracic, and abdominal aortic specimens may be obtained from human cadavers. Immediately After such collection, the aortas may be stored in phosphate buffered saline (PBS). For example, the time between autopsy and imaging possibly may not exceed about 48 hours. An exemplary bench-top system shown in FIG. 3 can be constructed to acquire laser speckle images of aortic plaques using optical fiber bundles.

Figure 3:
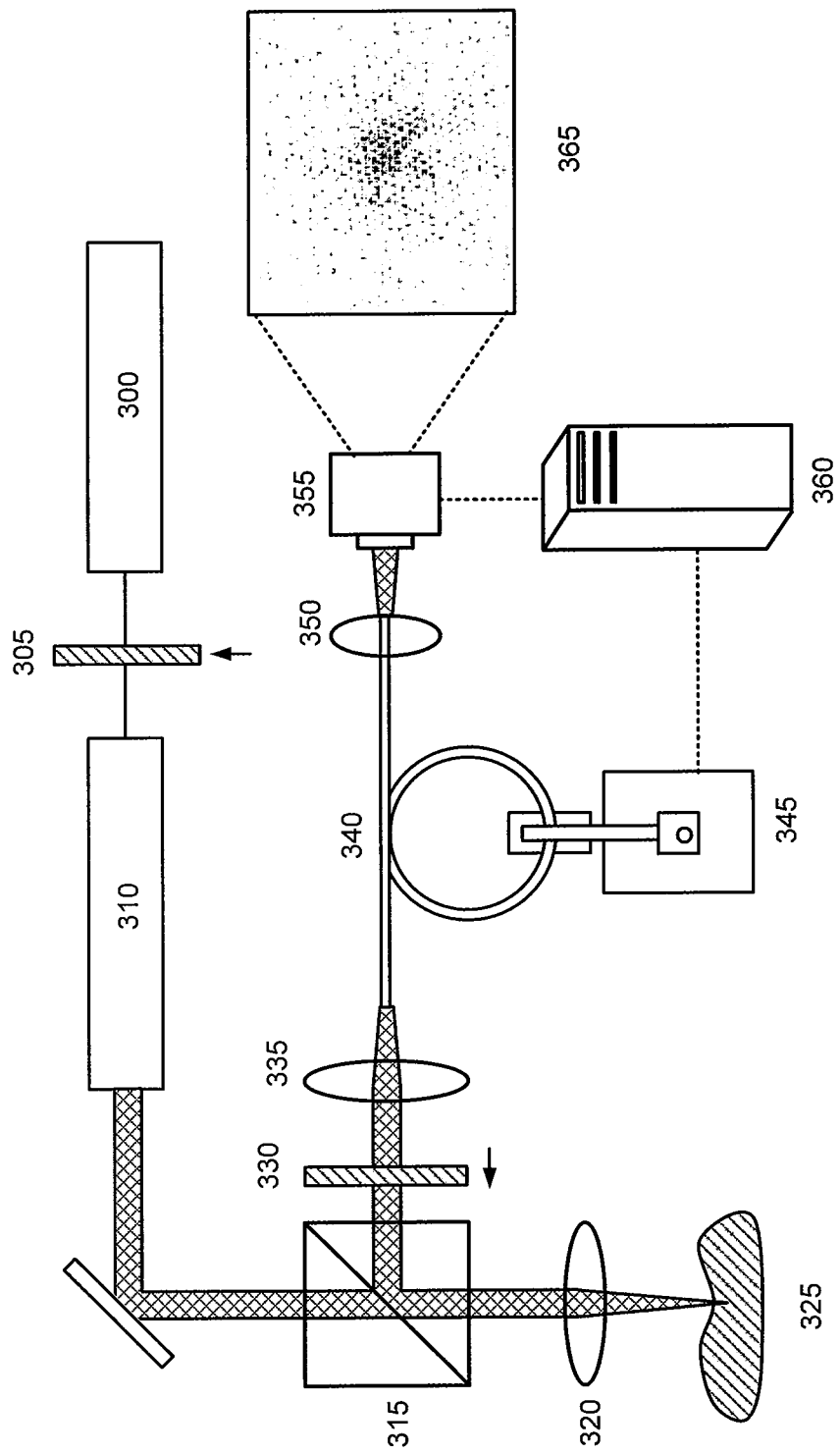
FIG. 3 is a schematic diagram of an arrangement for evaluating optical fiber bundles for LSI according to an exemplary embodiment of the present invention.

Two exemplary leached optical fiber bundles (Model #1119555, and Model #1119395, Schott, USA), and one commercially available angioscope (Vecmova, Fibertech, Japan) have been tested, the exemplary diagram of which is shown in FIG. 3. For example, the beam from a polarized Helium Neon laser (632 nm) 300 can be expanded (5×) 310, passed through a 50:50 beam splitter 315 and focused through a lens 320 to an approximately 50 μm diameter spot on the luminal surface of the plaque samples 325. Cross-polarized 305, 310 laser speckle patterns may be imaged (e.g., magnification=about 0.33) onto a distal end of a fiber bundle 340. For each bundle 340, the characteristic speckle size, likely determined by the resolution of the imaging system, can be approximately matched to the individual fiber size. Each fiber bundle may be inserted within a plastic tubing (e.g., diameter=about 3 mm) maintained at a radius of curvature of about 2 cm to mimic the curvature of the human LAD coronary artery.

A computer controlled motorized stage 345 can be used to control the motion of the optical fiber bundle. The motorized stage may be programmed (e.g., using a controller ESP 300, Newport) to mimic the coronary wall motion waveform over the cardiac cycle with a maximum peak-to-peak velocity of about 12 mm/s perpendicular to the axis of the bundle.[7] The proximal end of each bundle may be imaged using an objective lens 350 and images can be acquired using a CMOS camera 355 (e.g., Model #PL-A741, Pixelink, Ottawa, Canada). Time-varying laser speckle images 365 of aortic plaques may be obtained using each optical fiber bundle at a rate of about 240 frames per second. To provide accurate registration with histology, each imaging site can be marked with two India ink spots which delineated the diameter of the imaged speckle pattern on the lesion. A set of 18 randomly selected aortic plaque samples, can be imaged by all three bundles under stationary conditions and during bundle motion.

To demonstrate the efficacy of optical fiber bundle-based LSI for identifying high-risk NCFA's, the fiber bundle that may provide the highest tolerance to motion can be selected as described as follows. For example, using such exemplary bundle, about 74 aortic plaques were imaged during both stationary and moving conditions. Following imaging, all aortic plaques were fixed in 10% formalin, embedded and sectioned for histological processing. Sections were cut across the India ink spots and stained with Hematoxylin-Eosin and Trichrome stains. The histological sections were interpreted by a pathologist blinded to the LSI data. Plaques were classified into the following groups[1]: (i) intimal hyperplasia (IH), (ii) calcific (C), (iii) pathological intimal thickening (PIT), and (iv) necrotic-core fibroatheroma (NCFA). Morphometric measurements of fibrous cap thickness were obtained from the digitized histopathology slides. NCFA's with a minimum fibrous cap thickness<100 μm were further classified as high-risk NCFA's.[8]

Laser Speckle Analysis:

Time-varying laser speckle patterns obtained using the optical fiber bundles under stationary and moving conditions were analyzed using exemplary cross-correlation techniques to determine the speckle decorrelation time constant, $\tau$, which is inversely proportional to the rate of change of the speckle pattern.[3,4] The value of the normalized 2D cross-correlation between the first acquired speckle image and each image in the time-varying series was computed and plotted as a function of time to obtain the speckle temporal decorrelation curve for each sample. The time constant, $\tau$, for each plaque was computed by single exponential fitting of the region of the speckle decorrelation curve in which the cross-correlation value dropped to 75% of the maximum[4] for all bundles under stationary and moving conditions. Plaque decorrelation time constants were compared using linear regression analysis and paired t-tests for all three bundles.

The average difference (error) in time constant measurements under stationary and moving conditions was measured and expressed as a percentage of the time constant measured under stationary conditions. The fiber bundle with the highest tolerance to motion was selected as having the highest correlation, lowest error and minimal statistically significant difference in measurement of plaque time constants under stationary and moving conditions. The efficacy of this bundle for identifying high-risk NCFA's was tested during stationary conditions and bundle motion.

From histological diagnoses, the time constant value associated with each lesion was assigned to one of five plaque groups for most or all of 74 aortic plaques, and the average time constant and standard error for each group were computed. The differences between average time constant measurements for all plaque groups were compared using two-way (for plaque type and patient within each plaque group) ANOVA tests; the pair-wise comparisons between the high-risk NCFA group and other plaque groups were evaluated using the Dunnett's t-test. In most or all cases, a p-value<about 0.05 was considered statistically significant.

Figure 4:
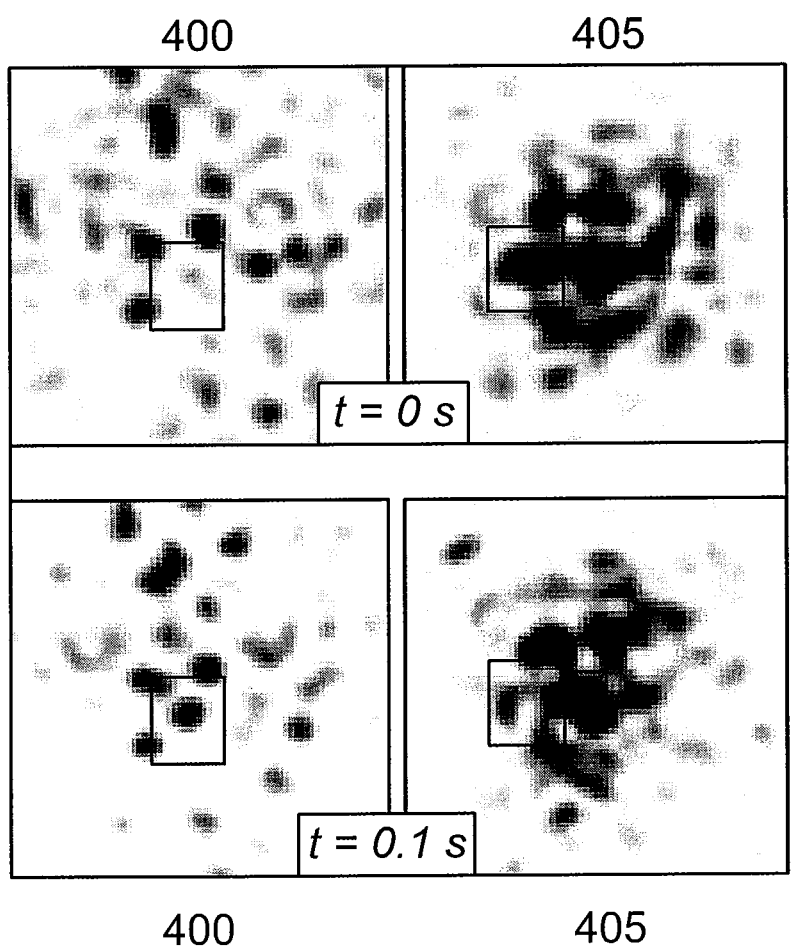
FIG. 4 are exemplary laser speckle images of static Teflon obtained using two high cross talk optical fiber bundles according to an exemplary embodiment of the present invention.

Exemplary preliminary results describing the use Optical fiber bundles for LSI are as follows:

Visual inspection of the speckle pattern confirmed an expectation that bundle motion interferes with the characteristic temporal evolution of laser speckle. FIG. 4 shows exemplary laser speckle images of a card paper using two high cross talk fiber bundles 400 and 405 in which there is significant leakage of light between individual fiber cores. FIG. 5 shows images of exemplary laser speckle patterns of a card paper obtained using a low cross talk leached fiber bundle, while the flexible shafts of the bundles were moved. Although the card paper exhibits a frozen speckle pattern when the system is stationary, rapid speckle motion is observed even with the slightest motion in the high cross talk fiber bundles as shown in FIG. 4 obtained about 100 ms after the onset of motion. The leached fiber bundle, on the other hand, showed high tolerance to bundle motion with negligible inter-fiber effect as seen in FIG. 5.

Figure 6A:
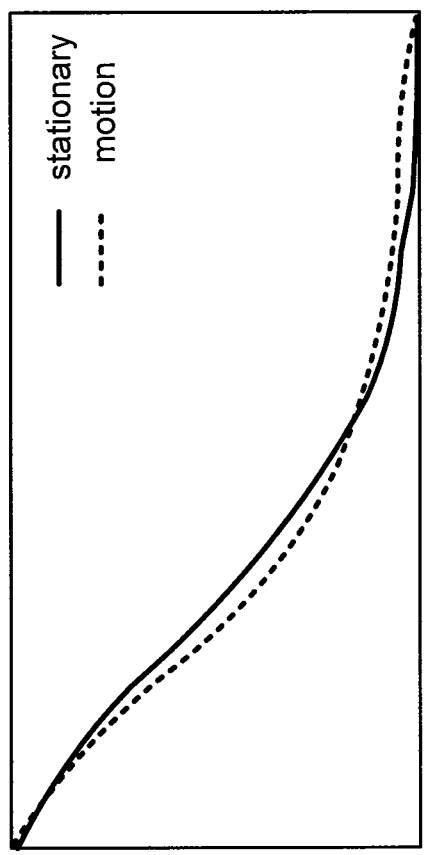
FIG. 6A is a graph showing exemplary speckle decorrelation curves measured from atherosclerotic plaque using a low cross talk optical fiber bundle according to an exemplary embodiment of the present invention.
Figure 6B:
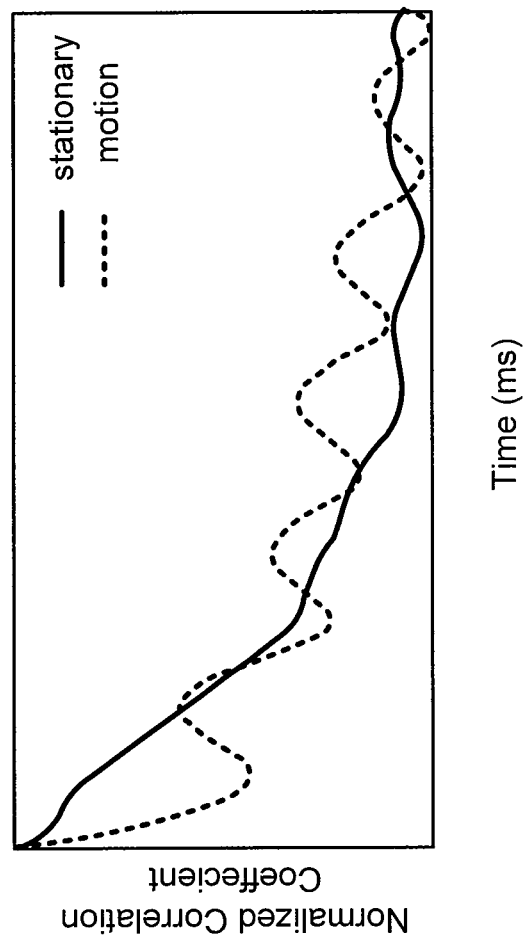
FIG. 6B is a graph showing exemplary speckle decorrelation curves measured from atherosclerotic plaque using a high cross talk optical fiber bundle according to an exemplary embodiment of the present invention.

Similar results can be observed in laser speckle patterns of atherosclerotic plaques obtained during fiber bundle motion. For example, graphs of exemplary normalized speckle decorrelation curves obtained from a fibrous plaque using the low cross talk optical fiber bundle are shown in FIG. 6A, and using high cross talk fiber bundle are shown in FIG. 6B. Normalized speckle decorrelation curves obtained using the high cross talk fiber bundle shown in FIG. 6B during stationary and moving conditions indicate larger differences resulting from the significant temporal modulation of the speckle pattern during motion with an error of ~80% in measuring the plaque time constant. On the other hand the normalized speckle decorrelation curves obtained from a low cross talk bundle as illustrated in FIG. 6A show a high correspondence during stationary and likely identical moving conditions of the fiber bundle. In such exemplary case, negligible inter-fiber effect during motion may result in, e.g., approximately a 7% error in measuring the plaque time constant.

Figure 7A:
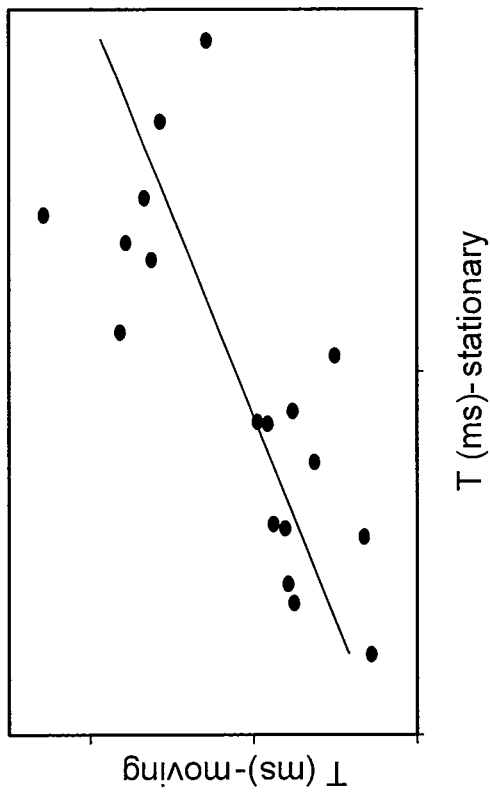
FIG. 7A is an image of a comparison of exemplary decorrelation time constants of atherosclerotic plaques using a low cross talk optical fiber bundle measured during moving and stationary conditions of the fiber bundle according to an exemplary embodiment of the present invention.
Figure 7B:
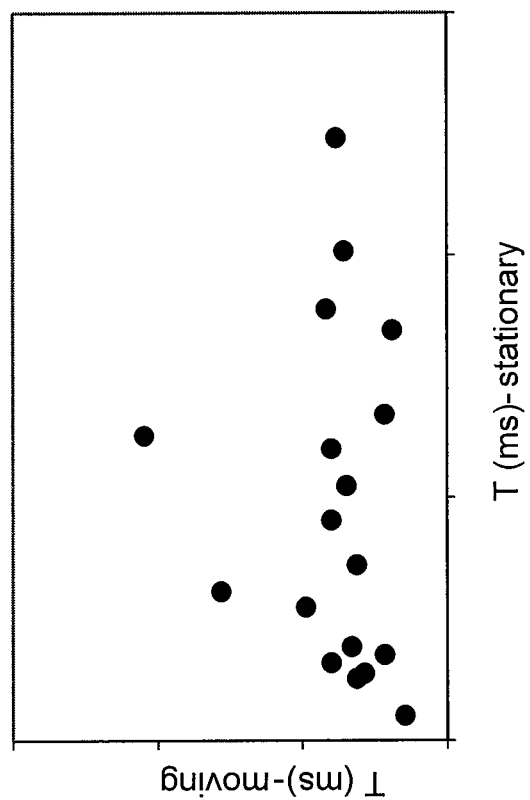
FIG. 7B is an image of a comparison of exemplary decorrelation time constants of atherosclerotic plaques using a high cross talk optical fiber bundle measured during moving and stationary conditions of the fiber bundle according to an exemplary embodiment of the present invention.

As shown in the graphs of FIGS. 7A and 7B, plaque time constants that can be measured while the bundles are stationary can be plotted against those measured during bundle motion for two bundles, with the results of the linear regression analysis and paired t—tests presented. For both the low cross talk bundle fiber bundles, an acceptable correlation can be found between plaque time constants measured during stationary and moving conditions, as illustrated in FIG. 7A. The low cross talk fiber bundle, provided a high correlation between time constants (e.g., R=0.75, p<0.0003) and low error (e.g., about 16%) in measuring plaque time constants during bundle motion, compared to stationary conditions. The results of paired t-tests for this bundle can show that plaque time constant measurements during motion may not be significantly different (e.g., p=0.21) from those measured by the stationary bundle. Using the high cross talk bundle, decorrelation time constants measured during bundle motion can show, e.g., no correlation with those measured under stationary conditions (e.g., R=0.1, p=0.69), as illustrated in FIG. 7B. Such exemplary bundle may provide, e.g., the highest error in measuring time constants during bundle motion compared to stationary conditions (e.g., 47%), and paired t-tests showed a statistically significant difference (e.g., p<0.003). Among the tested bundles, the leached fiber bundle with low cross talk may be the best combination of highest correlation (e.g., R=0.75), the lowest error (e.g., 16%) and least significant difference (e.g., p=0.21) in measuring plaque time constants during exemplary motion test, and was selected as having the highest tolerance to bundle motion.

Figure 8:
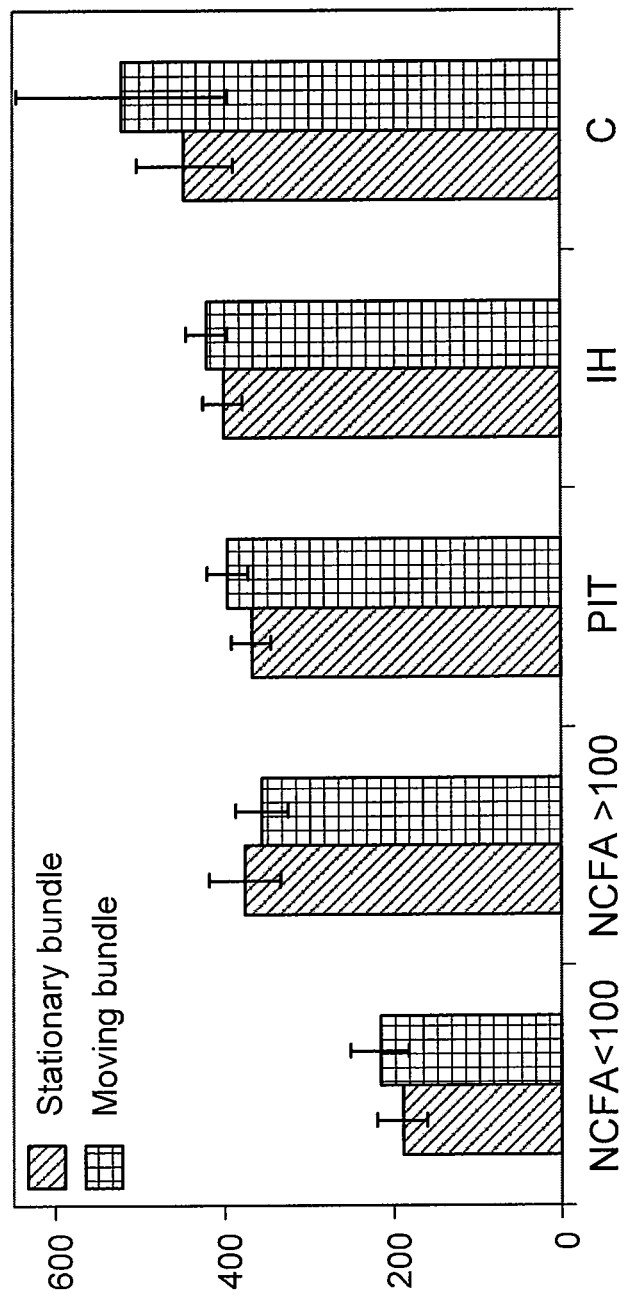
FIG. 8 is an exemplary graph of average decorrelation time constants of human atherosclerotic plaques obtained using a low cross talk optical fiber bundle during stationary and moving conditions of the fiber bundle according to an exemplary embodiment of the present invention.

The efficacy of the low cross talk leached fiber bundle for identifying high-risk NCFA's with LSI can then be evaluated using all 74 aortic specimens. The aortic specimens may be histologically classified as IH (n=17), C (n=9), PIT (n=29), NCFA with cap thickness>about 100 µm (n=11) and NCFA with cap thickness<about 100 µm (n=8). The exemplary average time constants which can be determined for the different plaque groups under both stationary and moving conditions are shown in a graph of FIG. 8. For example, paired t-tests showed that for all plaque groups, differences in decorrelation time constants measured during stationary and moving conditions may not statistically be significantly (e.g., p=0.07). The high-risk NCFA group with fibrous cap thickness<about 100 µm can have the lowest average time constant and the calcific group had the highest time constant for both the stationary and moving bundle conditions. In most or all cases, plaque time constants measured for the high-risk NCFA group can be significantly different from each of the other groups even during bundle motion (e.g., p<0.05). Additionally, paired t-tests showed no statistically significant differences in plaque time constants measured for the high-risk NCFA group under stationary and moving conditions of the bundle (e.g., p=43), suggesting that high-risk NCFA's can be identified in the presence of fiber bundle motion using the low cross talk leached fiber bundle.

The intricate interplay between biomechanical, compositional and morphological factors can influence the plaque stability. Exemplary techniques that measure these factors may be invaluable for identifying rupture-prone plaques, guiding treatment, and for investigating mechanisms associated with plaque stabilization therapies. Prior studies, conducted ex vivo, have shown that LSI measures an index of plaque viscoelasticity, which is related to plaque composition and morphology.[4]

While LSI shows great promise for assessing high-risk plaques, e.g., in order for it to be useful clinically, laser speckle measurements should likely be obtained from the coronary vasculature in vivo. Thus, it may be preferable to provide an exemplary embodiment of a catheter to illuminate and image diagnostic quality laser speckle patterns from the coronary wall.

The exemplary catheter can be similar in design to an angioscope, which may utilize a small diameter optical fiber bundle to illuminate and obtain images of the arterial wall. However, conventional angioscopes may be incapable of conducting LSI. Commercially available angioscopes, similar to certain angioscope, may often be designed to conduct white light endoscopy and provide high quality color images to evaluate coronary plaques in vivo. For such purpose, multi-core image fiber bundles may be used in commercial angioscopes in which multiple optical fiber cores are fused together in close proximity to achieve high fiber density in order to improve resolution. Due to the close proximity between fibers over the entire length of the image fiber, light may leak between the individual fiber cores. Unlike conventional angioscopy, laser speckle patterns, formed by interference of coherent light, are highly sensitive to motion. The high fiber density fused in close proximity over the length of the angioscope may contribute to leakage of light (crosstalk) between individual fibers which may be exacerbated during cardiac motion potentially corrupting laser speckle patterns of the arterial wall. Thus, the ability to conduct LSI via an intracoronary device may be dependent on the reliability of the optical wave guide to transmit arterial laser speckle images, e.g., in the presence of cardiac motion.

The exemplary leached fiber bundles may provide a high correlation in plaque time constants measured under stationary conditions and under conditions that simulated cardiac motion, likely indicating that these bundles may be suitable for intracoronary LSI. For example, leached fiber bundles may be composed of multiple optical fibers each consisting of a primary acid resistant cladding and a secondary acid soluble cladding that bonds the individual fiber elements.

The distal and proximal ends of the bundle are protected and the bundle can be immersed in an acid bath to leach away the secondary cladding producing a highly flexible fiber bundle. This exemplary process may result in a fiber bundle which is highly flexible with larger separation between individual optical fibers along the length of the bundle. This larger inter-fiber separation over the flexible part of the bundle may result in reduced inter-fiber cross-talk potentially allowing these bundles to be more conducive to the transmission of laser speckle images under motion conditions as compared to multi-core image fibers used in angioscopes.

With respect to the exemplary leached fiber bundles, the error in measuring plaque time constants under moving conditions may be significantly lower (e.g., ~16%) for the fiber bundle with the lowest partial core size (e.g., core area÷individual fiber area) of about 0.36. In addition, exemplary results of the paired t-tests showed no significant different in plaque time constants measured during stationary and moving conditions using this bundle, suggesting that the leached fiber bundle with low partial core size could be suitable for use in the intracoronary LSI device. Using such exemplary fiber bundle, high-risk NCFA's may be identified from a randomly selected group of 74 aortic plaques, even in the presence of motion (e.g., p<0.05 in all cases). The ability to conduct LSI using optical fiber bundles can depend on the inter-fiber leakage of light which is related to the separation between fiber cores. A leached optical fiber bundle with a low partial core size may elicit reduced cross-talk between fiber cores, thus allowing the reliable transmission of laser speckle patterns during motion.

In addition to the exemplary leaching process to obtain leached fiber bundles, another exemplary arrangement to reduce inter-core cross-talk can include packing an absorbing material to increase separation between individual fiber cores.

While commercially available angioscopes with low pixilation artifacts may be suitable for conducting white light angioscopy, it can be beneficial to optimize these angioscopes for LSI by incorporating low cross talk fiber bundles. According to one exemplary embodiment of the present invention, the distal and proximal end of the fiber bundles may be maintained fixed while the fiber bundle shaft can be moved using a computer-controlled motorized stage to mimic coronary motion over the cardiac cycle.

Under in vivo conditions, a motion of the distal end of the fiber bundle relative to the coronary wall, may also add an undesired speckle decorrelation that may reduce the diagnostic value of intracoronary LSI. One exemplary way of minimizing this effect can be to provide an intracoronary LSI device that can maintain a constant contact with the coronary wall during the imaging period, which may typically be less than about 100 ms. Certain well-established catheter designs used for intracoronary temperature measurement have been developed.[9,10] Thermography studies have demonstrated the utility and safety of contact-based intra-arterial catheters in which flexible thermosensors maintain contact with the vessel wall to measure local temperature changes associated with increased inflammation without requiring an interruption of coronary blood flow.

Alternately, cardiac gating methods may be employed which can provide for a sufficient temporal window during the resting phase of the cardiac cycle to obtain diagnostic quality speckle data. To obviate the influence of blood in the field of view, intracoronary saline flushing, which has been implemented for optical coherence tomography and angioscopy procedures to temporarily displace blood by injecting a bolus of saline,[11] can be utilized in conjunction with LSI to enable unobstructed imaging of the coronary wall.

Exemplary LSI Techniques in Presence of Blood:

Exemplary review described herein can evaluate the feasibility of LSI in the presence of blood.

Figure 9:
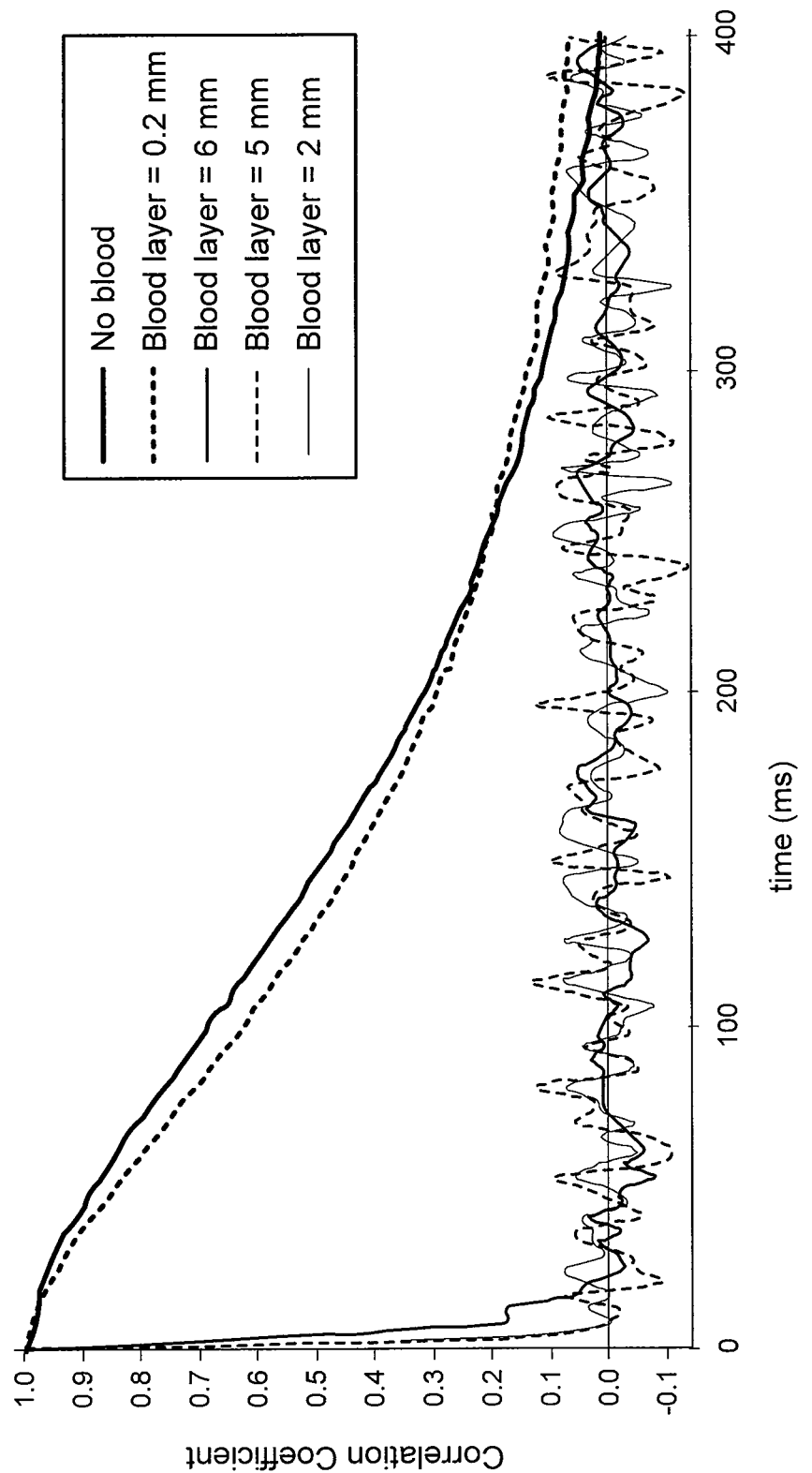
FIG. 9 is an exemplary graph of speckle decorrelation curves of an atherosclerotic plaque measured through different thicknesses of blood according to an exemplary embodiment of the present invention.

Effect of Blood on LSI Measurements:

A development of an intracoronary LSI catheter, similar in design to those used in thermography,[39,40] which contacts the arterial wall can be effectuated, thereby diminishing the influence of blood and potentially obviating the need for saline flushing. To provide preliminary data to evaluate the feasibility of this design, the influence of blood on LSI can be evaluated. The exemplary LSI procedures can be performed on a fibroatheroma placed within a transparent flow cell through an intervening layer of whole porcine blood (e.g., hematocrit (HCT)=32%). The thickness can be varied by raising the fibroatheroma through blood layer thickness different heights within the flow cell, and speckle decorrelation curves may be obtained as shown in the exemplary graph of FIG. 9. For intervening blood layers (~2-6 mm), due to on time constant multiple backscattering from blood cells, $\tau$ may be approximated to be that of whole blood (e.g., <approximately 4 ms). The exemplary results of the unpaired t-test showed that the average $\tau$ changed significantly in the presence of a blood layer (e.g., p<0.05). However, when the luminal surface of the plaque closely contacts the flow cell wall such that the intervening blood layer is reduced (e.g., 200 μm in this experiment), $\tau$ may not be significantly different (e.g., p=0.46) from that measured in the absence of blood.

These exemplary results can indicate that, as long as reasonably close contact (a few hundred microns) is maintained between the LSI catheter and the arterial wall, LSI may potentially be conducted in the presence of blood. Exemplary contact catheters can be provided for other optical imaging techniques and this level of close contact can be reliably achieved in coronary arteries.[41] An alternative exemplary method according to the present invention may be to conduct an exemplary intracoronary LSI procedure in conjunction with saline flushing as in other optical imaging techniques.[42]

To test the efficacy of the saline flushing approach, it is possible to perform an exemplary LSI procedure on four aortic plaques within the flow cell through, e.g., a 2 mm intervening layer of whole blood, serially diluted to different concentrations using phosphate buffered saline (PBS). It can be determined that, e.g., time constants, $\tau$, of aortic plaques measured by diluting blood to HCT can be <about 0.1% maybe similar to $\tau$ values measured without any intervening medium. Subsequently, the exemplary OCT imaging can be performed, and it may be determined that at HCT>about 0.03%, backscattering from blood cells can be evident in the exemplary OCT images. Previously, using intracoronary OCT, no backscattering from blood cells may have been observed. Since light over three locations across a 4 mm wide region of an FA for scattering due to blood likely does not affect LSI at a different thicknesses of intervening blood layers HCT<about 0.1% and saline purging apparently reduces the intracoronary HCT to <about 0.03%, it is possible to purge the coronary lumen so that LSI may be accurately conducted in patients. In summary, both the contact-catheter and saline flushing can be viable approaches to conduct intracoronary LSI.

Exemplary Design and Methods for Intravascular LSI catheter and System

Exemplary arrangements of optical waveguides to conduct intravascular LSI can be provided according to the exemplary embodiments of the present invention: For example, optical fiber bundle arrangements with low cross talk are capable of transmitting laser speckle images. Small diameter coherent optical fiber bundles can be drawn consisting of multiple fibers.

Figure 10A:
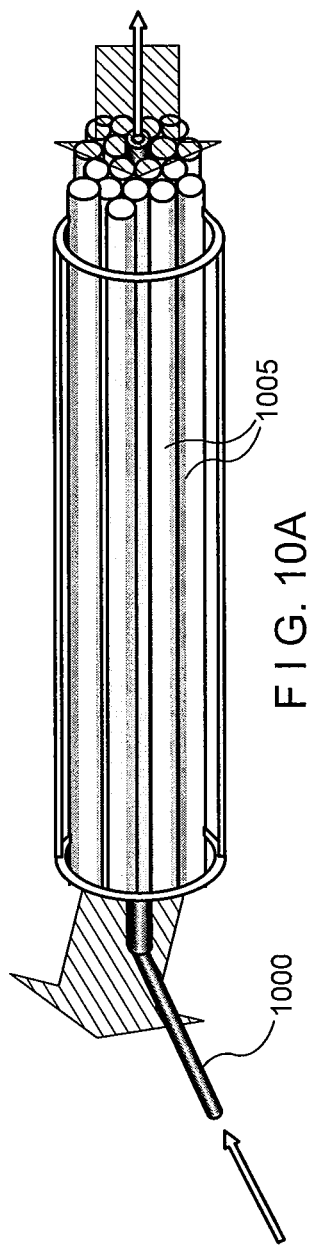
FIG. 10A is a side perspective view of a schematic diagram of a wave-guiding arrangement to conduct intravascular LSI according to an exemplary embodiment of the present invention.

In one exemplary embodiment of the present invention shown in FIG. 10A, a central light delivery fiber core 1000 of the fiber bundle arrangement can be a single mode or a multimode fiber to launch light which can be focused using a miniature lens towards the arterial wall. Surrounding single- or multimode fibers 1005 can transmit the speckle image.

Figure 10B:
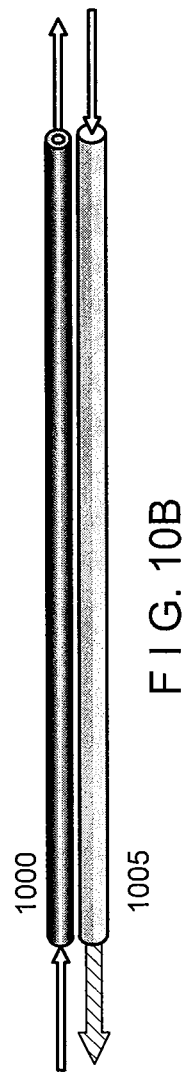
FIG. 10B is a side perspective view of a schematic diagram of a wave-guiding arrangement to conduct intravascular LSI according to another exemplary embodiment of the present invention.

In another exemplary embodiment shown in FIG. 10B, two optical fibers can be utilized to conduct intravascular LSI. One single mode or multimode can be used to forward focused or broad area illumination onto the arterial wall 1000 and another single or multimode fiber can be used to transmit the reflected light from the arterial wall 1005.

Figure 10C:
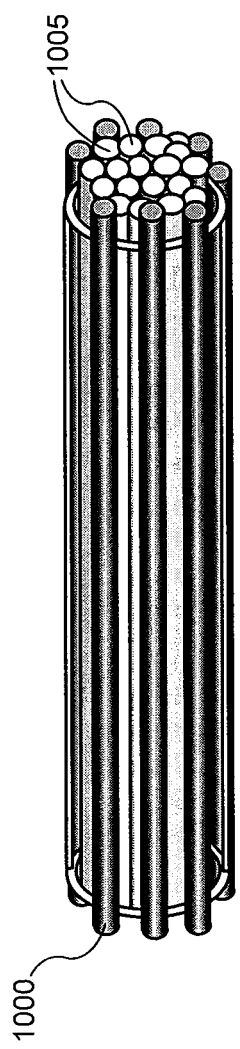
FIG. 10C is a side perspective view of a schematic diagram of a wave-guiding arrangement to conduct intravascular LSI according to yet another exemplary embodiment of the present invention.

In another exemplary embodiment shown in FIG. 10C, multiple single mode or multimode optical fibers 1000 can be used in an arrangement surrounding the collection fibers 1005 to conduct broad area illumination and collection of laser speckle patterns of the arterial wall.

Exemplary considerations for developing an imaging catheter capable of reliably transmitting laser speckle images of the coronary wall can be: (i) to enable evaluation of long (5.0 cm) segments of proximal main coronary arteries, (ii) to minimize the influence of blood on speckle modulation without interrupting blood flow, and (iii) to achieve sufficient motion stability during imaging.

Based on these exemplary considerations, an exemplary approach can be to construct an imaging catheter that maintains contact with the coronary wall during the LSI procedure, thereby obviating the influence of blood in the region of contact, and facilitating a sufficient coupling with the arterial wall to ensure adequate motion stability over the cardiac cycle.

One exemplary catheter design can be in view of an established design used for intracoronary temperature measurement. Thermography studies have demonstrated the utility and safety of contact-based intraarterial catheters in which flexible thermosensors maintain contact with the vessel wall to measure local temperature changes associated with increased inflammation without requiring interruption of coronary blood flow.[43] One exemplary design provides a catheter consisting of four nitinol prongs with dedicated thermistors which after engagement expand to maintain endoluminal surface during the procedure.[44] In another exemplary design, a contact basket catheter can be provided in which a nitinol basket equipped with flexible wires and thermosensors detects temperature changes of the vessel wall in the presence of blood flow without occluding the lumen designs have been successfully demonstrated in animal studies.[45] Clinical studies in several patients to date have exemplified the safety and efficacy of the contact-based design.[50]

One exemplary embodiment of the intravascular LSI catheter can utilize an exemplary basket catheter design. It is possible to provide a contact imaging basket catheter to conduct intracoronary LSI. It is possible to fabricate miniature optical imaging probes using a combination of in-house micromachining systems and, e.g., outsourcing Solid-Works CAD (SolidWorks Corporation, Concord, Mass.) schematics for precision machining.

Illustrations of one exemplary embodiment of the LSI catheter according to the present invention is provided in a schematic diagram of FIG. 11. For example, the target diameter of the intracoronary LSI catheter 1105 can be, e.g., less than about 1.5 mm. The catheter can be equipped with multiple (e.g., four) waveguide arrangements 1115. Each waveguide arrangement may be utilized to illuminate one quadrant of the coronary wall and to detect the speckle images that result. The waveguide arrangements can terminate in an expandable e.g., nitinol basket 1125 at the distal end of the catheter (see FIG. 11). The basket can contain four hollow expandable prongs, comprised of e.g., nitinol tubes with a central optical window 1120. The waveguide arrangements 1115 may be housed within the nitinol tubes of the basket and the imaging portion of each bundle may terminate at the central optical window. At its most distal end, a tapered connector 1130 can terminate the basket.

Once positioned within the coronary artery, the outer sheath 1110 may be retracted, the basket may expand, and the imaging portions of the fiber bundles may come into contact with the coronary artery wall. Proximal to the basket, a single wound, flexible cable, can envelop the four optical fiber bundles. To obtain LSI data at multiple locations along the artery, a remote, motorized computer-controlled translational stage 1100 connected to the proximal end of the wound cable can translate the deployed catheter along the coronary segment. Following the exemplary imaging procedure, the basket can be retracted into the catheter sheath so that the catheter can be withdrawn from the artery. A port to house a guide wire 1135 may be provided through the center of the catheter.

Low cross talk optical fiber bundles for example leached fiber bundles capable of transmitting laser speckle images can be incorporated within each basket prong. A custom-designed fiber bundles with minimal cross talk can be provided. Each prong of the basket catheter can be incorporated with one of multiple exemplary waveguide arrangements shown in FIGS. 10A, 10B and/or FIG. 10C.

Figure 12:
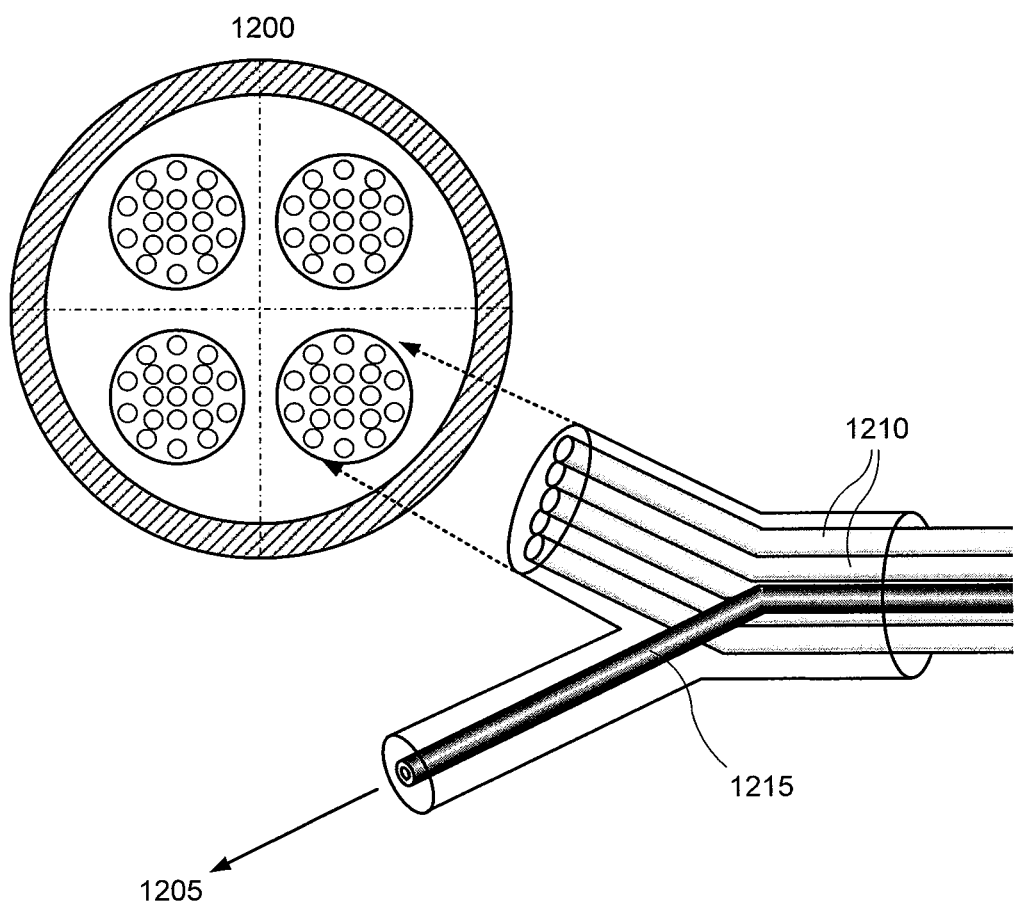
FIG. 12 is a diagram of the proximal end of the intracoronary LSI catheter (in a cut-away view and a side view) according to an exemplary embodiment of the present invention.

As shown in the schematic diagram in FIG. 12 of the exemplary embodiment of a catheter 1200 according to the present invention, on the proximal end thereof, the fiber bundles 1210 can be configured so that the light delivery fiber 1205 of each bundle may be separated from the collection fibers 1210. This exemplary arrangement can facilitate the use of separate illumination and collection ports.

Figure 13:
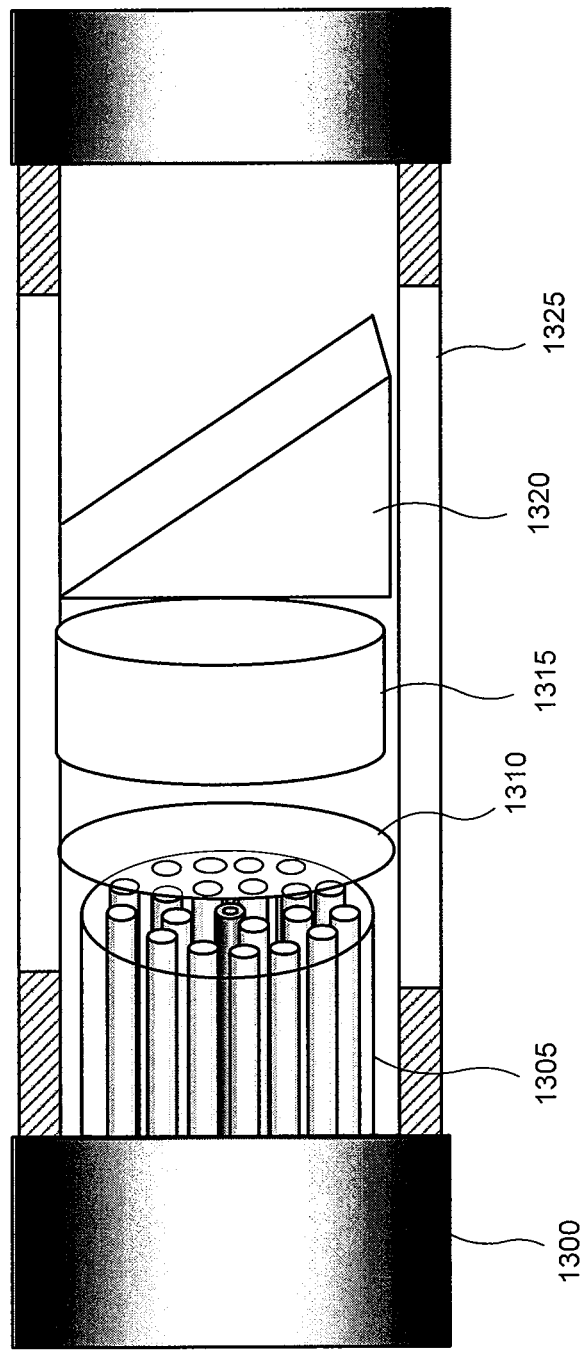
FIG. 13 is a side perspective view of the distal end of the intracoronary LSI catheter according to an exemplary embodiment of the present invention.

FIG. 13 shows a side view of an exemplary embodiment of the catheter according to the present invention, whereas the distal portion of each optical wave guide arrangement can contain miniature optics for focusing the incident light and imaging the speckle pattern through the optical window. For example, a distal end 1300, 1305 of the exemplary catheter can be affixed to the distal face of each wave guide arrangement to detect only cross-polarized light from the artery wall. An exemplary circular polarizer 1310 can be used to minimize specular surface reflections of the arterial wall. A miniaturized lens e.g., a gradient index (GRIN) microlens 1315 and reflective right angle prism 1320 may focus and direct light at ~90° from the catheter axis onto the vessel wall through the optical window 1325. Light remitted from the tissue can be imaged onto the fiber bundle face through the same optical components. The fiber bundle faces, polarizer, GRIN lens, and the prism may be provided with antireflection coatings to avoid reflections from the optical components.

Figure 14:
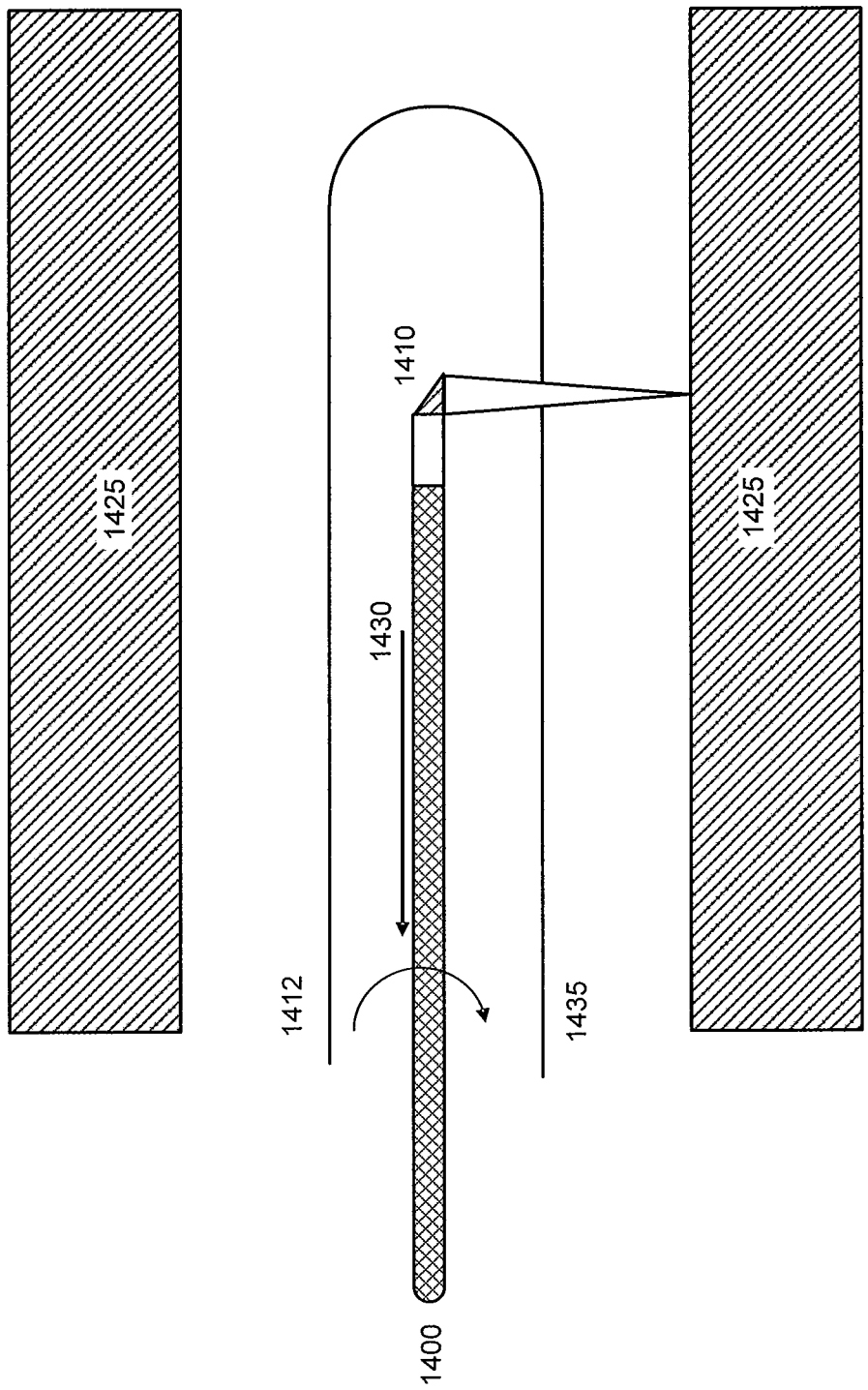
FIG. 14 a side view of an intracoronary LSI catheter arrangement according to another exemplary embodiment of the present invention.

FIG. 14 shows a side view of an exemplary embodiment of an intravascular LSI catheter according to the present invention in which the exemplary LSI catheter does not contact the vessel wall. For example, a single wave-guide arrangement 1400 includes one or multiple illumination and collection optical fibers (as shown in, e.g., FIGS. 10A, 10B and 10C) can be incorporated within a catheter sheath 1412. Focused or broad area illumination of the arterial wall 1425 can be conducted and speckle patterns can be imaged on to the distal end of the collection wave guiding arrangement using a distal optical arrangement 1410 described above in FIG. 13. An exemplary rotary junction can be used to rotate 1435 the intravascular catheter within the vessel lumen. The exemplary LSI procedure(s) can be conducted while a bolus of saline is flushed through the arterial wall.

FIG. 15 shows a side view of another exemplary embodiment of the intravascular LSI catheter according to the present invention in which a single wave guiding arrangement can be rotated within a balloon 1520 that is inflated to temporarily occlude coronary blood flow during the imaging duration. Similar element and features described above and labeled with numerals 1400, 1410, 1425 and 1430 are labeled with numerals 1500, 1510, 1525 and 1530, respectively, in FIG. 15.

Figure 16:
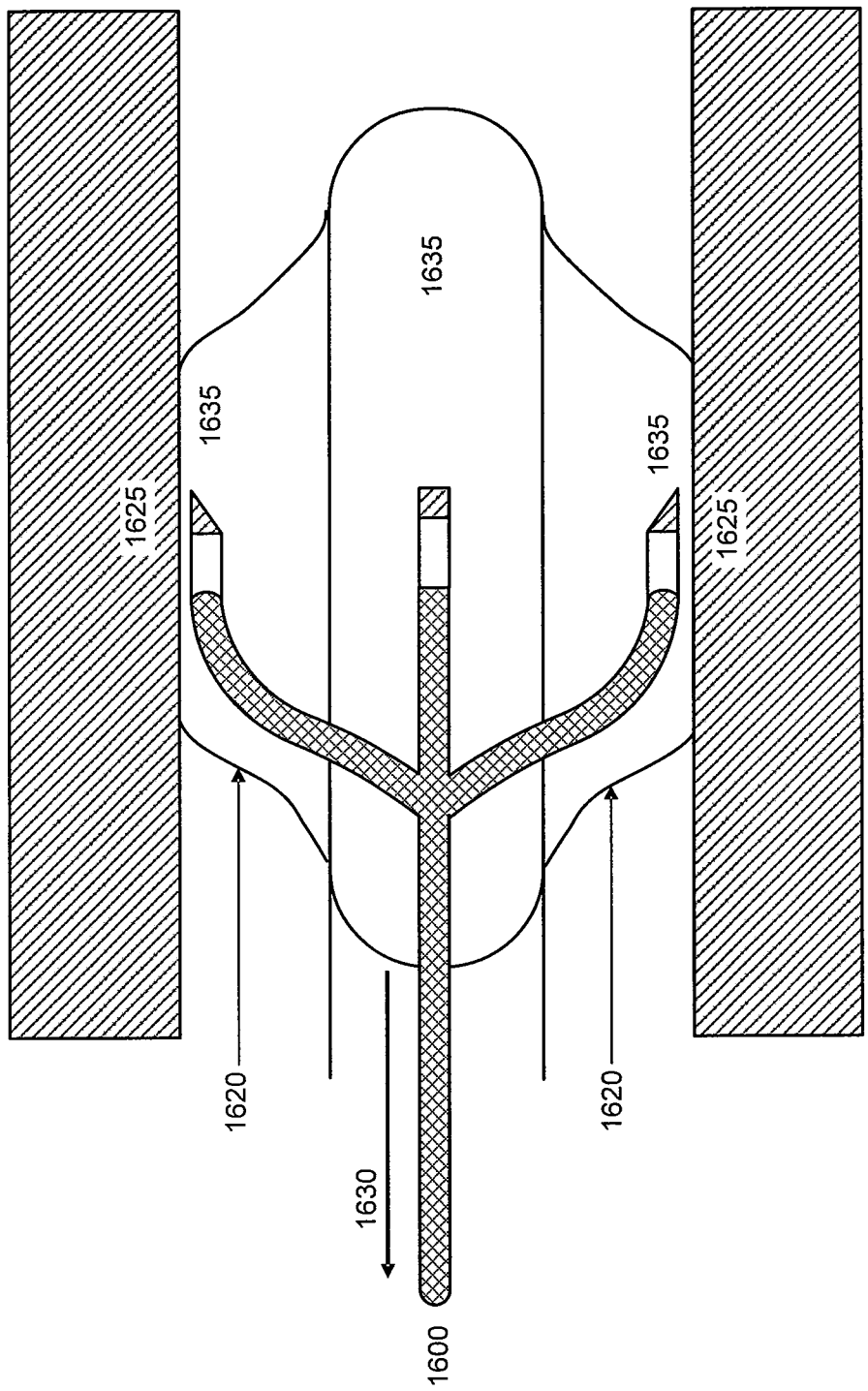
FIG. 16 a side view of the intracoronary LSI catheter arrangement according to still another exemplary embodiment of the present invention.

FIG. 16 shows a side view of still another exemplary embodiment of the intravascular LSI catheter according to the present invention in which multiple prong waveguiding arrangements 1635 are affixed within a clover shaped balloon 1620 which partially occludes blood flow during imaging and maintains contact with the arterial wall 1625 to minimize the effect of cardiac motion on the transmission of laser speckle patterns. Similar element and features described above and labeled with numerals 1400, 1410 and 1430 are labeled with numerals 1600, 1610 and 1630, respectively, in FIG. 16.

An exemplary embodiment of an LSI cart system and instrumentation can be as follows. For example, an exemplary LSI system can be assembled and incorporated within a portable medical cart for ease of use in the catheterization suite. The exemplary system may contain a coherent light source. In a multiple prong embodiment, light from the laser can be coupled into a single-mode fiber, connected to a single mode fiber-optic star coupler that splits the input light equally into multiple optical fibers. Each output port of the star coupler may be connected to the illumination fiber of each waveguiding arrangement (see FIGS. 11A, 11B, 11C and 16).

Figure 17:
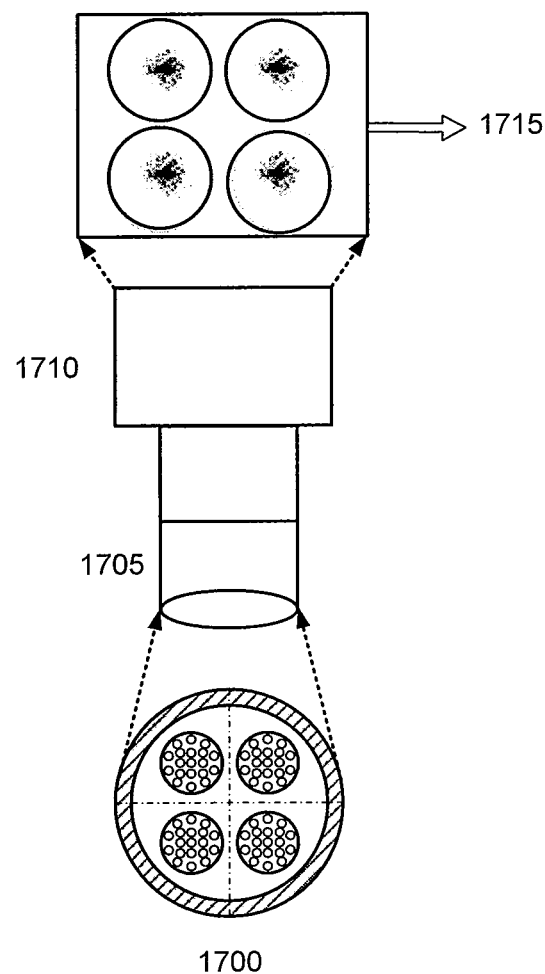
FIG. 17 is a side view of a schematic diagram of an exemplary embodiment of the LSI catheter at the proximal end for performing the LSI image detection according to an exemplary embodiment of the present invention.

At the collection end of an exemplary embodiment of a system according to the present invention as shown in a schematic diagram of FIG. 17, a high-speed, triggerable digital CCD camera 1710 can be incorporated in the LSI cart. A relay lens 1705 may image the collection port onto the CCD camera so that laser speckle images transmitted by the multiple waveguide arrangements may be simultaneously detected 1715. A Camera Link interface capable of high data transfer rate of may be used to transfer image data to a computer in real time.

Exemplary Imaging.

According to one exemplary embodiment of the present invention, each imaging location along the vessel, time-varying laser speckle images may be acquired for at least about 40 ms. This acquisition time can provide sufficient data for NCFA characterization and may be sufficiently short to allow screening of large coronary segments. A custom-built pullback device using a computer-controlled stage may be affixed to the wound cable at the proximal end of the catheter. Basket pullback can be conducted in exemplary discrete steps (e.g., 0.1-2 mm) at a rate of up to 5 mm/s and speckle data may be obtained over at least 40 ms at each step when the catheter is stationary.

Exemplary Methods and Techniques

The exemplary methods and techniques according to the present invention that can be utilized to design, provide, and verify the exemplary intracoronary LSI catheter and system are described herein.

Exemplary Fiber Bundle:

A variety of both off-the-shelf and custom fiber optic bundles can be obtained and tested for their suitability for transmitting laser speckle images. First, off-the-shelf bundles with different core:cladding ratios can be obtained from Schott Inc. It is possible to test crosstalk by illuminating one of the fibers and detecting light leakage in the cladding and adjacent fibers. The testing environment can include an apparatus for bending the fiber bundle to evaluate crosstalk as a function of radii of curvature (e.g., 3-10 cm). It is possible to additionally test the capability of the bundle to transmit dynamic and static speckle images of scattering phantoms while moving the flexible length of the bundle (5-20 mm/s) and comparing time constants to those obtained by a stationary bundle and with a free space system. Once exemplary specifications are evaluated using off-the-shelf bundles, it is possible to then design and have custom fiber bundles fabricated. The custom end. bundles can have separate central illumination and collection fibers with sufficiently low crosstalk. The custom fiber bundles may be tested using the same methods. It is believed that ~10% deviation in time constants measured through the fiber bundle can be obtained, compared to those measured with an exemplary free space system.

Exemplary LSI Catheter Optics:

A variety of different lenses may be simulated, including GRIN and aspheric micro-optical lenses. Optimization can be performed to minimize aberrations through different optical window designs and to increase FOV. Following the optimized design and selection as shown in an exemplary embodiment of FIG. 16: An exemplary photograph of configuration and components, optical elements may be purchased and coronary circulation assembled onto the fiber bundle. Light can be transmitted through the central phantom fiber onto static and dynamic scattering phantoms. As above, it is possible to i) compare time constants obtained with the bundle and optics, with the bundle straight and with coronary circulation phantom, and ii) compare time constant of phantoms measured through exemplary bundle and optics with that obtained by exemplary free-space system. Success can be defined as a deviation of <10% between these measurements.

Exemplary Intracoronary Basket or Balloon:

The exemplary intracoronary basket or balloon may be designed and constructed based on exemplary specifications (see FIGS. 11A, 11B, 11C, 15 and 16). In the exemplary basket embodiment, an imaging window can be provided by a notch in the nitinol tubes at the center of the basket, where light can be transmitted. The distal optics may be fed through the hollow nitinol prongs so that they are located and oriented for optimal coupling upon contact with the vessel wall. Following correct positioning of the optics, such optics can be affixed to the prongs by applying a small drop of optically transparent epoxy in the notch. Alternatively, they can be affixed in place distal to the bundle and a thin (few microns) transparent sleeve can be placed over the notch. Both of these exemplary methods can be used, and it is believe that they are viable options for affixing fiber miniature optics at the distal end of catheters. Similarly, exemplary waveguide arrangements can be affixed within the balloon to maintain arterial contact. After the optics are incorporated, it is possible to test the performance of the assembled catheter in the same manner as exemplary methods described above. As described herein, it is possible to define success as a deviation in time constant measurements of <about 10%.

Exemplary Basket or Balloon Catheter Contact Testing:

Close (e.g., few hundred micrometers) contact between the catheter and the arterial wall may be preferable to conduct the exemplary LSI procedure during blood flow. The surface contact of the basket at the imaging site may be evaluated in excised cadaveric arterial specimens. Contact can be measured using optical frequency domain imaging (OFDI),[44] a cross-sectional optical imaging technique with high speed, high-resolution (e.g., 10 µm), and a large ranging depth (e.g., about 10 mm). The experimental exemplary arrangement according to the present invention to test catheter contact is depicted in a diagram of FIG. 18.

The intracoronary LSI catheter 1810 may be introduced into the coronary artery 1815 and the exemplary distal basket or balloon can be engaged while OFDI monitoring 1805 is performed external to the vessel and coincident with LSI imaging location. Precise registration between the OFDI beam and the LSI site is possible since the LSI illumination beam may be visible through the adventitia of the artery. Catheter contact can be evaluated under at least three conditions: (a) during vessel deformation, (b) in the presence of blood, and (c) during catheter pullback. To evaluate the effect of vessel deformation, an automated syringe pump may inject saline 1800 to cause a 10% radial deformation of the arterial wall mimicking the extent of physiological coronary deformation.[48] Exemplary pressure measurement 1825 may be conducted during the experiment. The response time of the nitinol basket or balloon construct to conform to arterial deformation can be evaluated by varying the saline infusion may be used to test intracoronary LSI system and rates from about 1-10 cc/s.

Further, whole porcine blood can be injected into the artery during OFDI monitoring 1805 and scattering due to blood in the region of basket contact may be evaluated. Finally, the custom-built motorized pullback device can be used to linearly translate the LSI intracoronary catheter to evaluate the effect of pullback rates on basket-to-wall contact. This testing may be performed, e.g., in two phases of catheter development, during design optimization of the nitinol basket and after completion of the catheter. Success can be defined as, e.g., <about 200 µm spacing between the basket prongs and the arterial wall for greater than 80% of the pullback length.

Exemplary LSI System:

Exemplary optical components for imaging the fiber bundle collection port may be designed and optimized with ZEMAX and subsequently fabricated and assembled. The laser, star coupler, collection optics, CCD, pullback device, and computer can be integrated in a portable cart. The computer or another processing arrangement may also include a data acquisition board for digitizing the EKG during speckle pattern acquisition. Software can be developed for controlling the motors, reading and storing motor encoder positions, real-time speckle analysis, and displaying data in a various formats for ease of interpretation.

Figure 18:
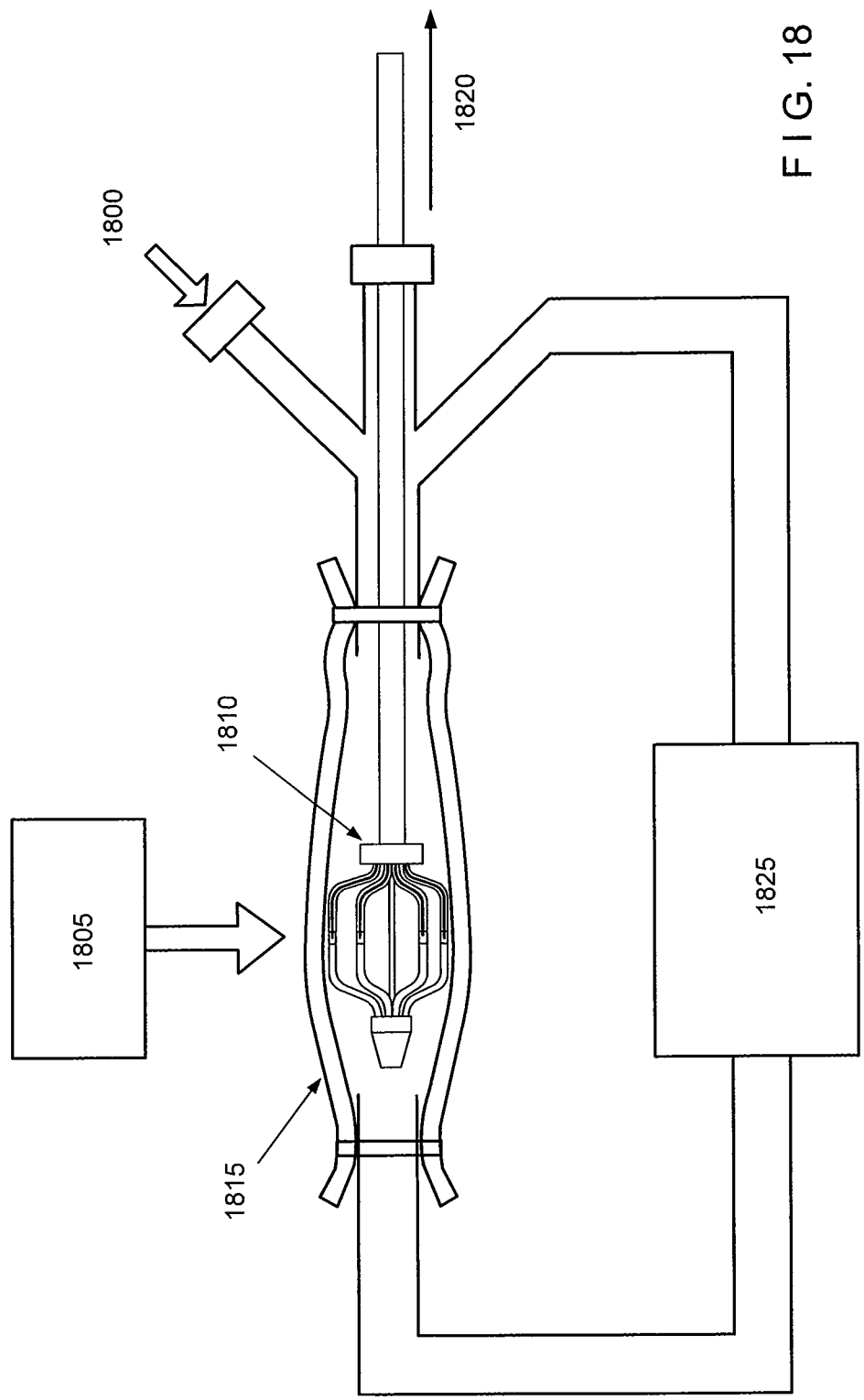
FIG. 18 is a schematic diagram of an exemplary arrangement of intracoronary LSI system and catheter in excised arteries for testing and/or evaluating the exemplary embodiments.

Exemplary Diagnostic Performance of Intracoronary LSI Ex Vivo:

Cadaver coronary arterial segments may be excised during autopsy and prepared for LSI testing using the experimental configuration, as shown in the diagram of an exemplary embodiment illustrated in FIG. 18. For example, segments can be immersed in phosphate buffered saline and warmed to 37° C. Time-varying laser speckle images may be obtained over 5 cm arterial segments with the LSI catheter at about 1.0 mm increments, using a measurement duration at each site of 40 ms. Intracoronary LSI can be conducted (a) without blood, (b) in the presence of blood, and (c) during arterial deformation. At each imaging site, the arterial specimens may be marked at each quadrant along the adventitial aspect of the specimen using different colored ink spots for precise registration of each quadrant with histology. Marking can be facilitated by observation of the laser light through the arterial wall.

The speckle decorrelation time constant may be determined at each spatial location from the normalized cross-correlation of time-varying laser speckle images. The arterial specimens can be fixed in Formalin and prepared for histological processing. Using the Histopathologic diagnosis as the gold standard, the sensitivity and specificity of intracoronary LSI for identifying necrotic core fibroatheromas with thin fibrous caps (<65 µm) can be evaluated under all three experimental conditions. Diagnostic performance targets to determine success in identifying TCFA's may be based on a presumed intra-plaque and intra-patient correlation of approximately 50%, with an estimated TCFA prevalence of about 3%.

(A) Exemplary Performance Targets for Intracoronary LSI Catheter and System (B) Exemplary Performance Targets for Diagnostic Performance of Intracoronary LSI Catheter and System

| Performance Target | Value | Justification and Verification Method |
| --- | --- | --- |
| Fiber bundle crosstalk | <10% | Based on certain preliminary studies, it is believed that cross talk of <10% between fibers with a radius of curvature of 3 cm can be sufficient to satisfy exemplary requirements for intracoronary LSI. It is possible to measure fiber crosstalk by illuminating a single fiber and detecting light leakage in the cladding and adjacent fibers for different radii of curvature as described above in Specific method 1. |
| Catheter size | <1.5 mm (4.7 F) | The catheter can be designed with a target size of <1.5 mm. Each of the four expandable prongs of the distal basket may have a diameter of 350 µm, with a 250 µm guide wire through the center of the catheter. When engaged, the distal basket can be designed to expand and conform to the coronary wall. |
| Imaging Rate | 2000 frames/s | A high-speed CCD camera (Mikrotron MC 1310) may be incorporated in the system capable of acquiring 512 × 512 pixel images at 2000 frames/s over 40 ms at each imaging site. |

-continued

| Performance Target | Value | Justification and Verification Method |
|---|---|---|
| Date storage rate | 200 MB/s | The speckle data from the CCD camera can be digitally stored in real-time. This data storage rate is more than sufficient to recover all images at video rate. |
| Field of View (FOV) | ~500 μm | Using Monte Carlo simulations (FIG. 9), this FOV can be more than sufficient to allow evaluation of the critical superficial ~400 μm of the arterial wall |
| Imaging time | Tens of seconds | Catheter pullback may be conducted in discrete steps (0.1-2 mm), and speckle data can be acquired at each step for 40 ms. A pullback rate of 5 mm/s may allow imaging of a typical 5 cm artery in tens of seconds. |
| Basket catheter contact | <200 μm | Catheter contact can be measured using OFDI as described above in Specific method 4. Success may be defined as <200 μm spacing between prongs and arterial wall for >80% of the pullback length. |
| LSI catheter compared with free space system | ~10% deviation in τ | As described in the Specific methods, time constants of scattering phantoms measured through the LSI catheter can be compared with the free space system (see FIG. 2). Based on exemplary preliminary experiments using low crosstalk fiber bundles, it is anticipated ~10% deviation between time constants measured in the two cases. |
| Sensitivity for detecting TCFA's. Specificity for detecting TCFA's | ~95% ± 7% (no blood) ~90% ± 10% (with blood) ~90% ± 10% (no blood) ~85% ± 12% (with blood) | Comparison of time constant measured by intracoronary LSI may be statistically compared with Histological diagnoses to determine sensitivity and specificity for TCFA detection without blood and in the presence of blood. These expected values are determined based on exemplary sample size (1000 plaques) and TCFA prevalence (e.g., 3%) calculations, accounting for intra-plaque and intra-patient correlation of 50%. Success is defined by the feasibility of detecting TCFA's since this is clinically most significant. |

Exemplary Intracoronary LSI Feasibility Review in Living Swine Coronary Xenograft Model Exemplary Overview:

The exemplary intracoronary LSI catheter and system described herein can be tested in a pilot animal study to determine feasibility of conducting LSI in vivo. Rationale for human-to-swine coronary xenograft model: A selection of animal model can be motivated by two important preferences. First, feasibility of intracoronary LSI can be preferably tested on evaluating human coronary atherosclerosis. Second, testing should be performed in a living animal model under conditions of hemodynamics and cardiac motion that closely approximate human coronary physiology. Based on these preferences, the exemplary approach is to use a human-to-swine coronary xenograft model that allows imaging of human coronaries under physiological conditions similar to those encountered in humans, the exemplary utilization being shown in FIG. 19. The exemplary model shown in FIG. 19 has been successfully utilized with intracoronary optical techniques.

Exemplary Methods for In Vivo Animal Testing

Figure 19:
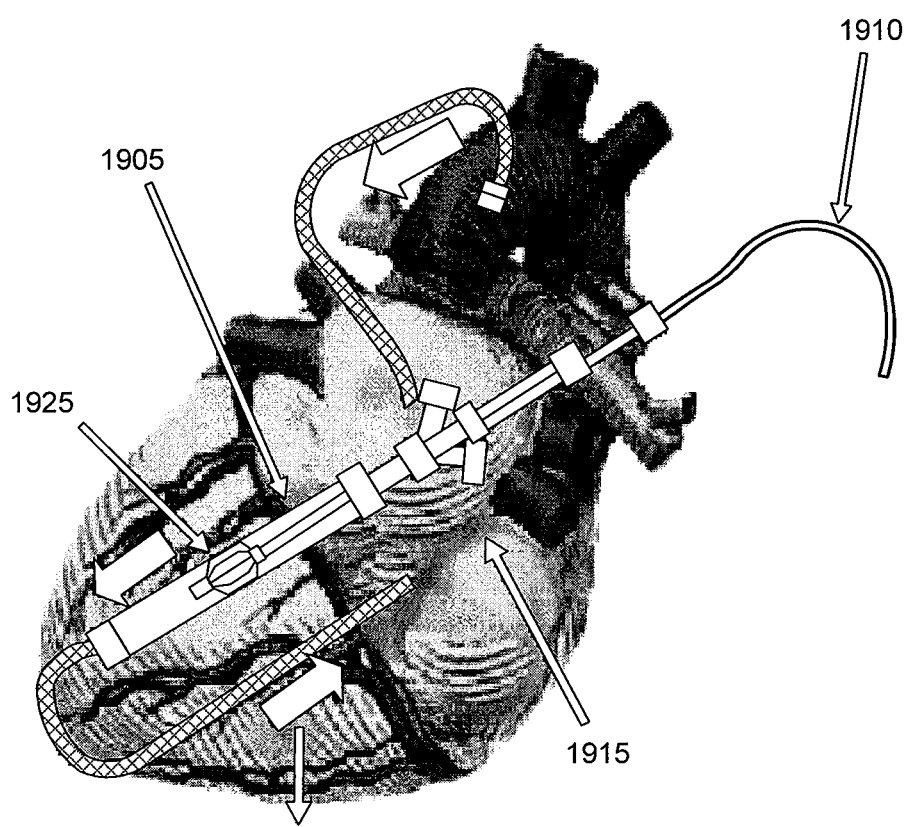
FIG. 19 is a diagram of an arrangement to test intracoronary LSI system and catheter using in vivo animal experiments according to the exemplary embodiment of the present invention.

Exemplary Human Coronary Xenograft Model:

Yorkshire swine can be used in the study. Normal swine may provide controls and additional swine can be grafted with human cadaveric coronary artery xenografts. In brief, human cadaveric hearts may be obtained at autopsy and screened using angiography to identify proximal coronary arteries with disease. Once selected, as shown in FIG. 19, exemplary candidate coronary segments 1905 (~5 cm) can be prosected off the cadaver heart, the side branches ligated, and luer locks sutured to the ends of the grafts. In each coronary segment, adventitial fat may be removed and discrete imaging sites can be randomly selected along the length and marked with India ink spots on the artery. The swine may be anesthetized and the heart surgically exposed.

The cadaveric coronary graft (with ink marks facing upwards) can be surgically implanted to the ascending aorta at the proximal end and sutured to the left ventricle to ensure mechanical coupling with the beating swine heart 1915 as shown in FIG. 19. A "Y" connector with a valve and guide-port may be connected proximal to the coronary graft for saline administration and introduction of the exemplary LSI catheter 1910.

Exemplary In Vivo Intracoronary LSI:

The intracoronary LSI procedure may be conducted the anesthesized swine with simultaneous EKG monitoring and recording. For example, FIG. 19 shows an exemplary embodiment of a configuration of the LSI catheter to be used in the swine heart during the imaging procedure. A guide catheter and guide wire can be introduced into the coronary graft through the guide port of the "Y" connector. The exemplary LSI catheter may be inserted over the guide wire and advanced into the coronary graft. After the catheter is positioned within the coronary graft, the outer catheter sheath can be retracted and the distal imaging basket may expand to contact the coronary endoluminal surface. At the proximal end, the exemplary LSI catheter can be affixed to a computer controlled pull-back device incorporated in the portable LSI system. Imaging may be performed at each of the 10 discrete sites. At each LSI site, the catheter can be positioned such that the visible laser beam observed through the coronary wall at one basket prong overlaps with the fiducial mark and the pullback motor coordinates may be recorded.

The exemplary intracoronary LSI procedure can be conducted (a) without interruption of blood flow, and (b) with administration of saline flush. The EKG may trigger the CCD camera to begin acquisition of the first frame on the R-wave, followed by asynchronous acquisition of subsequent frames at a rate of about 2000 frames/s for a duration of 5 seconds. Next, a 5 cc saline flush can be administered while the exemplary LSI procedure is repeated at the each site. Following imaging of the first coronary graft, the guide wire and LSI catheter may be retracted through the guideport and a second graft can be imaged.

Figure 20A:
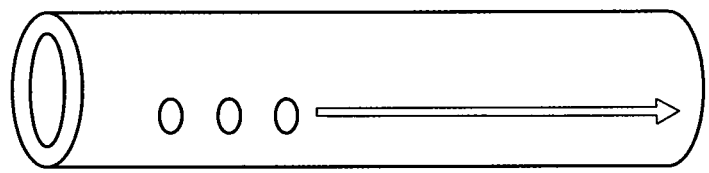
FIGS. 20A-20C are illustrations of exemplary implementations for providing computer controlled pull-back device in operation according to an exemplary embodiment of the present invention.
Figure 20B:
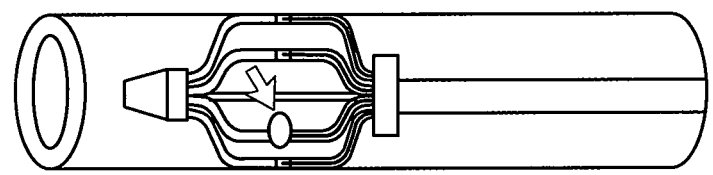
Figure 20C:
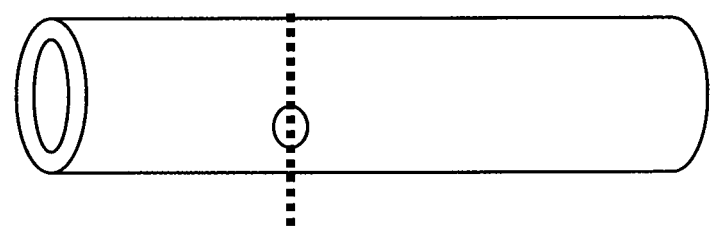

The influence of heart rate on the exemplary LSI procedure performance may be evaluated by administering 10 μg/kg/min of dobutamine, which has been previously described in the swine animal model to cause ~50% increase in heart rate.[45] LSI imaging can be repeated as above after heart rate is stabilized. In the two normal control swine, the exemplary intracoronary LSI procedure may be similarly repeated to image the native LAD and LCx arteries. In the control arteries, ink marking of discrete locations is difficult on the beating heart. Instead, the computer controlled pullback device can pull back as shown in FIGS. 20A-20C. The exemplary catheter can be operated, e.g., at a rate of 5 mm/s through 10 discrete steps spaced 5 mm apart during the performance of the exemplary LSI procedure in humanswine, while the exemplary intracoronary LSI procedure is performed, e.g., over 5 seconds at coronary xenograft model. each location. In many or all cases, the linear translator position and the EKG may be digitally recorded throughout the procedure.

Exemplary Histological Processing and Analysis:

Following exemplary imaging technique(s), the swine can be sacrificed by the intravenous administration of sodium pentobarbital (120 mg/kg) with heparin (100 U/kg). The coronary segments may be fixed in 10% formalin, embedded and sectioned using standard Histology techniques. Cross-sectional sections (thickness=4 μm) can be cut across each ink mark, stained with H & E, Trichrome and Picrosirius stains (PSR) (for collagen), and interpreted by a pathologist blinded to the LSI data. All coronary sections may be broadly characterized into two groups: NCFA and nonnecrotic core plaques. Fibrous cap thickness in the NCFA set and collagen content in all plaques can be determined from digitized histology sections.[46,47]

Exemplary LSI Data Analysis:

Due to its high clinical significance, the performance of intracoronary LSI in identifying NCFA's may be determined. For example, a large number (e.g., 260) of coronary sites can be analyzed, including 100 human cadaveric coronary sites in the xenograft model and 160 sites in the control native coronaries (e.g., 10 sites/artery×2 arteries×4 quadrants×2 control swine). Exemplary time constants may be measured by exponential fitting of the normalized cross-correlation data for each coronary site over a duration of 40 ms by previously described exemplary LSI techniques.

Using Histopathologic diagnosis as the gold standard, the sensitivity and specificity for identifying NCFA's can be evaluated for the following conditions: (a) in the presence of blood, (b) during saline administration, and (c) following dobutamine administration. Exemplary diagnostic performance targets to determine success in identifying NCFA's may be based on a presumed intra-plaque and intra-patient correlation of approximately 50%, with an estimated prevalence of 10%. Statistical significance to achieve discrimination of NCFA's under all conditions can be evaluated using two-way ANOVA tests: success may be defined by $p<0.05$. The exemplary relationships between LSI time constants with NCFA cap thickness and collagen content in all plaques measured under the above conditions can be determined using linear regression analysis. In all cases, success may be defined by a statistically significant (e.g., $p<0.05$) good correlation (e.g., $R>0.6$) between measurements.

Exemplary Variation in Time Constants Over Cardiac Cycle:

The influence of cardiac phase over the cardiac cycle on LSI measurements can be evaluated by measuring time constants within a windowed duration of 40 ms over 5 s (~5 cardiac cycles). The mean, $\tau$, and standard deviation, $\sigma\tau$, in time constants measured over the cardiac cycle may be determined for all plaques. The cardiac motion over 40 ms may not influence a significant variation in time constants and it is anticipated an average variation in $\tau$ of ~10% over the cardiac cycle. However, this variation may be dependent on tissue type, since the rate of Brownian motion during arterial deformation is dependent on composition. For example, plaques containing a compliant lipid core may present a higher $\sigma\tau$ over the cardiac cycle as compared with stiffer fibrous plaques. The exemplary standard deviation, $\sigma\tau$, may potentially provide an additional diagnostic metric for plaque discrimination.

Figure 21A:
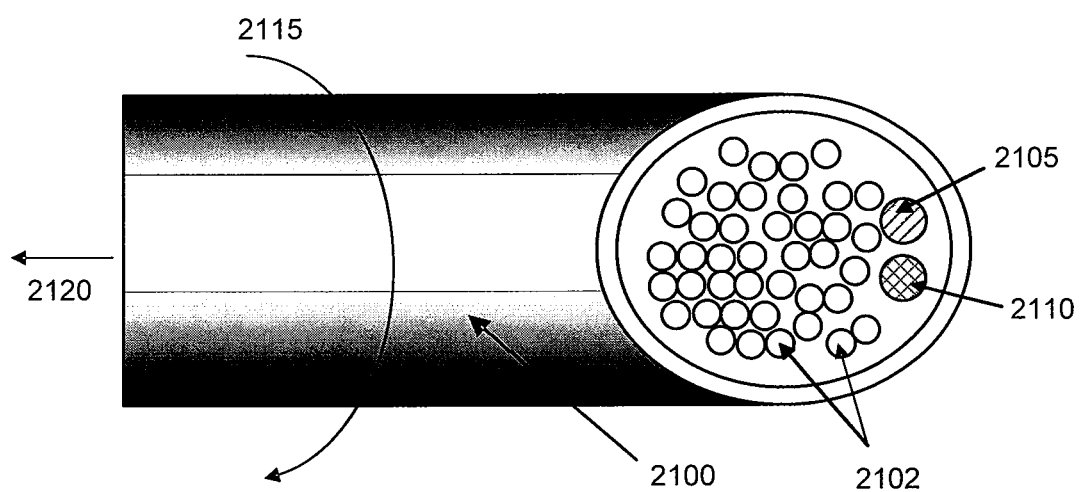
FIGS. 21A-21B are illustrations of exemplary implementations to conduct LSI in conjunction with other exemplary intra-coronary techniques.
Figure 21B:
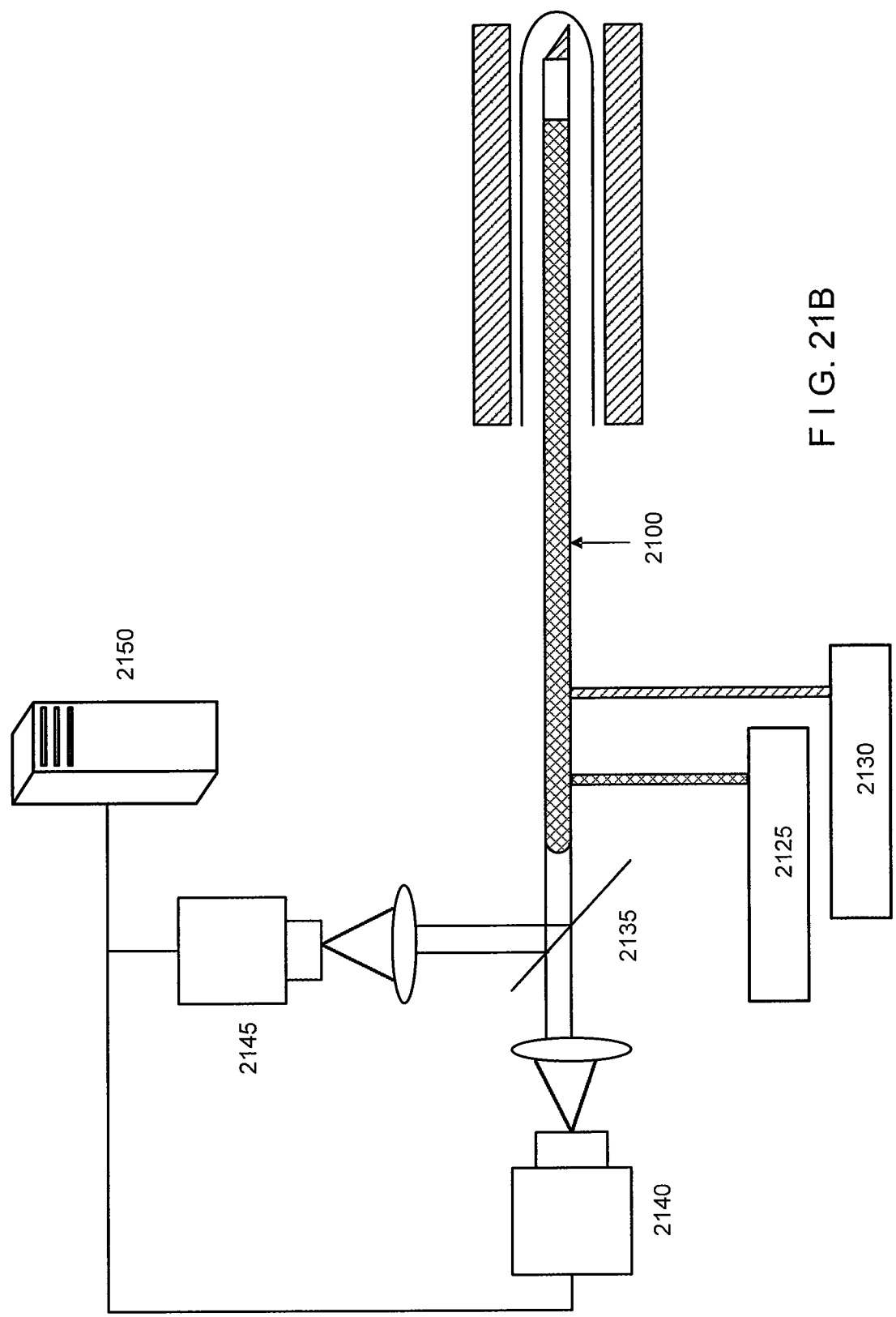

Exemplary Clinical Implementation of Intra-Coronary LSI:

Intracoronary LSI may be implemented in the catheterization suite as a stand alone technique as described in the embodiments above or as an adjunct to other intra-vascular techniques such as angioscopy. In one embodiment, LSI may be conducted simultaneously with angioscopy through a single catheter. A cross-sectional view of an exemplary catheter to simultaneously perform angioscopy in conjunction with LSI is shown in FIG. 21A. An exemplary catheter 2100 may consist of low cross talk optical waveguides consisting of multiple fiber cores 2102 for collecting both angioscopy and laser speckle patterns of the arterial wall may be incorporated. Optical wave guides may be incorporated for illumination using white light such as a xenon lamp source to conduct angioscopy 2105 and a waveguide for coherent light illumination 2110 to conduct LSI. The exemplary configuration of the waveguide arrangement may include at least one of the exemplary embodiments described herein and shown in FIGS. 10A, 10B and/or 10C. The exemplary rotation 2115 and/or pullback 2120 of the catheter may be facilitated either manually or utilizing a rotary junction and/or a motorized translational stage. An exemplary system to conduct angioscopy in conjunction with LSI is shown in FIG. 21B. A light source such as a xenon source 2125 and a coherent light source 2130 may be utilized in the exemplary system for illumination through the catheter 2100. LSI and angioscopy images may be collected simultaneously via the collection port. A dichroic mirror 2135 may be utilized in conjunction with a color camera to capture angioscopy images at video rate and a high speed camera 2145 to capture coherent laser speckle patterns at high frames rates. A Camera Link interface capable of high data transfer rate of may be used to transfer image data to a computer 2150 in real time.

Exemplary Performance Targets

| Performance Target | Value | Justification and Verification Method |
|---|---|---|
| Variation in LSI time constant measurements | ~10% | It is anticipated that about ~10% deviation in time constants comparing LSI conducted in the presence of blood to imaging during the administration of a saline flush. Additionally, since cardiac motion over 40 ms may not cause a significant variation in time constants, it is anticipated that ~10% deviation in time constants measured at resting heart rate compared with those measured at increased heart rate following dobutamine administration. |

-continued

| Performance Target | Value | Justification and Verification Method |
|---|---|---|
| In vivo detection of NCFA's: -sensitivity - specificity | 90% ± 10%<br>85% ± 15% | Comparison of time constant measured by intracoronary LSI can be statistically compared with Histological diagnoses to determine sensitivity and specificity for NCFA detection in vivo. These expected values are determined based on exemplary sample size (260 plaques) and NCFA prevalence (10%) calculations. Success may be defined by the feasibility to attain these values in the presence of blood or during administration of a saline flush. |
| Intracoronary LSI relationships with collagen content and NCFA cap thickness | R > 0.6<br>(p < 0.05) | Collagen content and NCFA cap thickness measured from Histological sections can be compared with time constant measurements. |

Exemplary Significance:

It is possible to provide an intracoronary LSI catheter and system according to an exemplary embodiment of the present invention to enable evaluation of long coronary segments in vivo. Thus, it is possible to determine composite metrics based on plaque viscoelasticity, composition and morphology to predict the propensity of plaque rupture in patients. Similar techniques using intravascular LSI can be utilized for evaluating plaque in other vasculature such as the carotid arteries, peripheral arteries and renal arteries.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

Exemplary References cited Herein are as follows:

[1] Virmani R, Kolodgie F D, Burke A P, Farb A, Schwartz S M. Lessons from sudden coronary death: a comprehensive morphological classification scheme for atherosclerotic lesions. Arterioscler Thromb Vasc Biol. 2000; 20:1262-75.

[2] Schroeder A P, Falk E. Vulnerable and dangerous coronary plaques. Atherosclerosis. 1995; 118 Suppl:S141-9.

[3] Bauriedel G, Hutter R, Welsch U, Bach R, Sievert H, Luderitz B. Role of smooth muscle cell death in advanced coronary primary lesions: implications for plaque instability. Cardiovasc Res. 1999; 41:480-8.

[4] Newby A C, Zaltsman A B. Fibrous cap formation or destruction—the critical importance of vascular smooth muscle cell proliferation, migration and matrix formation. Cardiovasc Res. 1999; 41:345-60.

[5] Rekhter M D, Hicks G W, Brammer D W, Hallak H, Kindt E, Chen J, Rosebury W S, Anderson M K, Kuipers P J, Ryan M J. Hypercholesterolemia causes mechanical weakening of rabbit atheroma: local collagen loss as a prerequisite of plaque rupture. Circ Res. 2000; 86:101-8.

[6] Slager C J, Wentzel J J, Gijsen F J, Thury A, van der Wal A C, Schaar J A, Serruys P W. The role of shear stress in the destabilization of vulnerable plaques and related therapeutic implications. Nat Clin Pract Cardiovasc Med. 2005; 2:456-64.

[7] Schartl M, Bocksch W, Koschyk D H, Voelker W, Karsch K R, Kreuzer J, Hausmann D, Beckmann S, Gross M. Use of intravascular ultrasound to compare effects of different strategies of lipid-lowering therapy on plaque volume and composition in patients with coronary artery disease. Circulation. 2001; 104:387-92.

[8] Aikawa M, Rabkin E, Okada Y, Voglic S J, Clinton S K, Brinckerhoff C E, Sukhova G K, Libby P. Lipid lowering by diet reduces matrix metalloproteinase activity and increases collagen content of rabbit atheroma: a potential mechanism of lesion stabilization. Circulation. 1998; 97:2433-44.

[9] Libby P, Aikawa M. Mechanisms of plaque stabilization with statins. Am J. Cardiol. 2003; 91:4B-8B.

[10] Aikawa M, Libby P. Lipid lowering reduces proteolytic and prothrombotic potential in rabbit atheroma. Ann NY Acad Sci. 2000; 902:140-52.

[11] Fukumoto Y, Libby P, Rabkin E, Hill C C, Enomoto M, Hirouchi Y, Shiomi M, Aikawa M. Statins alter smooth muscle cell accumulation and collagen content in established atheroma of watanabe heritable hyperlipidemic rabbits. Circulation. 2001; 103:993-9.

[12] Richardson P D, Davies M J, Born G V. Influence of plaque configuration and stress distribution on fissuring of coronary atherosclerotic plaques. Lancet. 1989; 2:941-4.

[13] Loree H M, Kamm R D, Stringfellow R G, Lee R T. Effects of fibrous cap thickness on peak circumferential stress in model atherosclerotic vessels. Circ Res. 1992; 71:850-8.

[14] Ohayon J, Teppaz P, Finet G, Rioufol G. In-vivo prediction of human coronary plaque rupture location using intravascular ultrasound and the finite element method. Coron Artery Dis. 2001; 12:655-63.

[15] Tang D, Yang C, Kobayashi S, Ku D N. Effect of a lipid pool on stress/strain distributions in stenotic arteries: 3-D fluid-structure interactions (FSI) models. J Biomech Eng. 2004; 126:363-70.

[16] Schaar J A, De Korte C L, Mastik F, Strijder C, Pasterkamp G, Boersma E, Serruys P W, Van Der Steen A F. Characterizing vulnerable plaque features with intravascular elastography. Circulation. 2003; 108:2636-41.

[17] Lee R T, Yamamoto C, Feng Y, Potter-Perigo S, Briggs W H, Landschulz K T, Turi T G, Thompson J F, Libby P, Wight T N. Mechanical strain induces specific changes in the synthesis and organization of proteoglycans by vascular smooth muscle cells. J Biol Chem. 2001; 276: 13847-51.
[18] Lee R T, Berditchevski F, Cheng G C, Hemler M E. Integrin-mediated collagen matrix reorganization by cultured human vascular smooth muscle cells. Circ Res. 1995; 76:209-14.
[19] Liebson P R, Klein L W. Intravascular ultrasound in coronary atherosclerosis: a new approach to clinical assessment. Am Heart J. 1992; 123:1643-60.
[20] Rogers W J, Prichard J W, Hu Y L, Olson P R, Benckart D H, Kramer C M, Vido D A, Reichek N. Characterization of signal properties in atherosclerotic plaque components by intravascular MRI. Arterioscler Thromb Vasc Biol. 2000; 20: 1824-30.
[21] Yabushita H, Bouma B E, Houser S L, Aretz H T, Jang I K, Schlendorf K H, Kauffman C R, Shishkov M, Kang D H, Halpern E F, Tearney G J. Characterization of human atherosclerosis by optical coherence tomography. Circulation. 2002; 106: 1640-5.
[22] Brezinski M E, Tearney G J, Bouma B E, Izatt J A, Hee M R, Swanson E A, Southern J F, Fujimoto J G. Optical coherence tomography for optical biopsy. Properties and demonstration of vascular pathology. Circulation. 1996; 93:1206-13.
[23] Jang I K, Bouma B E, Kang D H, Park S J, Park S W, Seung K B, Choi K B, Shishkov M, Schlendorf K, Pomerantsev E, Houser S L, Aretz H T, Tearney G J. Visualization of coronary atherosclerotic plaques in patients using optical coherence tomography: comparison with intravascular ultrasound. J Am Coll Cardiol. 2002; 39:604-9.
[24] Tearney G, J., Bouma B E. Atherosclerotic plaque characterization by spatial and temporal speckle pattern analysis. Optics Letters. 2002; 27:533-535.
[25] Schmermund A, Rodermann J, Erbel R. Intracoronary thermography. Herz. 2003; 28:505-12.
[26] Stefanadis C, Toutouzas K, Tsiamis E, Pitsavos C, Papadimitriou L, Toutouzas P. Identification and stabilization of vulnerable atherosclerotic plaques: the role of coronary thermography and external heat delivery. Indian Heart J. 2001; 53:104-9.
[27] Uchida Y, Fujimori Y, Hirose J, Oshima T. Percutaneous coronary angioscopy. Jpn Heart J. 1992; 33:271-94.
[28] Casscells W, Hathorn B, David M, Krabach T, Vaughn W K, McAllister H A, Bearman G, Willerson J T. Thermal detection of cellular infiltrates in living atherosclerotic plaques: possible implications for plaque rupture and thrombosis. Lancet. 1996; 347:1447-51.
[29] Moreno P R, Lodder R A, Purushothaman K R, Charash W E, O'Connor W N, Muller J E. Detection of lipid pool, thin fibrous cap, and inflammatory cells in human aortic atherosclerotic plaques by near-infrared spectroscopy. Circulation. 2002; 105:923-7.
[30] de Korte C L, van der Steen A F, Cespedes E I, Pasterkamp G. Intravascular ultrasound elastography in human arteries: initial experience in vitro. Ultrasound Med Biol. 1998; 24:401-8.
[31] Schmitt J M. OCT elastography: imaging microscopic deformation and strain of tissue. Opt. Express. 1998; 3:199-211.
[32] Mason T G, Weitz D A. Optical measurements of frequency-dependent linear viscoelasticity moduli of complex fluids. Physical Review Letters. 1995; 74:1250-1253.
[33] Palmer A, Xu J, Kuo S C, Wirtz D. Diffusing wave spectroscopy microrheology of actin filament networks. Biophys J. 1999; 76:1063-71.
[34] Yamada S, Wirtz D, Kuo S C. Mechanics of living cells measured by laser tracking microrheology. Biophysical Journal. 2000; 78:1736-1747.
[35] Goodman J W. In: Statistical Optics: Wiley Interscience; 2000: 347-356.
[36] Nadkarni S K, Bouma B E, Helg T, Chan R C, Halpern E, Chau A, Minsky M, Motz J, Houser S L, Tearney G, J. Characterization of atherosclerotic plaques by laser speckle analysis. Circulation. 2005; (in press).
[37] Nadkarni S K, Bouma B E, Helg T, Chan R, Halpern E, Chau A, Minsky M S, Motz J T, Houser S L, Tearney G J. Characterization of atherosclerotic plaques by laser speckle imaging. Circulation. 2005; 112:885-92.
[38] Lewis J P. Fast Template Matching. Vision Interface. 1995: 120-123.
[39] Verheye S, De Meyer G R, Van Langenhove G, Knaapen M W, Kockx M M. In vivo temperature heterogeneity of atherosclerotic plaques is determined by plaque composition. Circulation. 2002; 105:1596-601.
[40] Naghavi M, Madjid M, Gul K, Siadaty M S, Litovsky S, Willerson J T, Casscells S W. Thermography basket catheter: in vivo measurement of the temperature of atherosclerotic plaques for detection of vulnerable plaques. Catheter Cardiovasc Interv. 2003; 59:52-9.
[41] Motz, J T, Puppels G J, Waxman S, Bakker Schut T C, Marple E. Nazemi J. Chau A. Gardecki J A<Brennan J F, Tearney G J. Percutaneous intracoronary Raman spectroscopy. In: Cardiovascular Revascularization Therapies. Washington, D.C.; 2007: 813
[42] Jang I K, Tearney G J, MacNeill B, Takano M, Moselewski F, Iftima N, Shishkov M, Houser S, Aretz H T, Halpern E F, Bouma B E. In vivo characterization of coronary atherosclerotic plaque by use of optical coherence tomography. Circulation. 2005; 111:1551-5.
[43] Madjid M, Willerson J T, Casscells S W. Intracoronary thermography for detection of high-risk vulnerable plaques. J Am Coll Cardiol. 2006; 47:C80-5.
[44] Yun S H, Tearney G J, de Boer J F, Iftima N, Bouma B E. High-speed optical frequency domain imaging. Optics Express. 2003; 11:2953-2963.
[45] Handke M, Heinrichs G, Magosaki E, Lutter G, Bode C, Geibel A. Three-dimensional echocardiographic determination of cardiac output at rest and under dobutamine stress: comparison with thermodilution measurements in the ischemic pig model. Echocardiography. 2003; 20:47-55.
[46] Whitaker P. Polarized light microscopy in biomedical research. Microscopy and Analysis. 1995: 15-17.
[47] Nadkarni S K, Pierce M C, Park B H, de Boer J F, Whitaker P, Bouma B E, Bressner J E, Halpern E, Houser S, Tearney G J. Measurement of collagen and smooth muscle cell content in atherosclerotic plaques using polarization-sensitive optical coherence tomography. J Am Coll Cardiol. 2007 (in press).

What is claimed is:
1. An apparatus for intracoronary laser speckle imaging, comprising:
a light-delivery optical fiber configured to illuminate a coronary wall with laser light that scatters from the coronary wall to form laser speckle patterns;
a light-collecting fiber bundle configured to transmit laser speckle patterns formed by the scattered light, wherein fibers in the light-collecting fiber bundle are separated by at least 3 times a width of at least one fiber core so as to reduce crosstalk between fibers down to no greater than 10 percent of collected light; and a detector configured to detect the laser speckle patterns transmitted by the light-collecting fiber bundle;
wherein the apparatus is configured to diminish effects of intervening blood on detection of laser speckle patterns by allowing no more than 200 μm of blood to flow between the light-collecting fiber bundle and the coronary wall.

2. The apparatus of claim 1 wherein fibers in the light-collecting fiber bundle include a primary acid-resistant cladding and a secondary acid-soluble cladding that bonds individual fibers.

3. The apparatus of claim 1 wherein the light-collecting fiber bundle fiber bundle has a partial core size no greater than 0.36, wherein the partial core size is core area divided by individual fiber area.

4. The apparatus of claim 1 wherein the light-collecting fiber bundle is leached.

5. The apparatus of claim 1 wherein the crosstalk is measurable by illuminating one fiber in the light-collecting fiber bundle and detecting light leakage in fibers adjacent to the illuminated fiber.

6. The apparatus of claim 1 further including a catheter and a motorized, computer-controlled translation stage for translating the catheter along a coronary segment.

7. A method for speckle imaging, comprising:
using a light-delivery optical fiber to illuminate an anatomical structure with coherent light that scatters from the anatomical structure to form a speckle pattern;
using a light-collecting fiber bundle to collect scattered light and transmit the speckle pattern formed by the scattered light, wherein fibers in the light-collecting fiber bundle are separated by at least 3 times a width of at least one fiber core so as to reduce crosstalk between fibers; and
to diminish effects of intervening blood on detection of the laser speckle pattern, allowing no more than 200 μm of whole blood to flow between the light-collecting fiber bundle and the anatomical structure.

8. The method of claim 7 wherein the light-collecting fiber bundle reduces a measurable crosstalk down to no greater than 10 percent of light collected by the light-collecting fiber bundle.

9. The method of claim 8 wherein the light-collecting fiber bundle includes cladding, and wherein the crosstalk is measurable by illuminating one fiber in the light-collecting fiber bundle and detecting light leakage in the cladding and fibers adjacent to the illuminated fiber.

10. The method of claim 8 wherein a radius of curvature of fibers in the light-collecting fiber bundle ranges from three centimeters to ten centimeters.

11. The method of claim 7 wherein one or more fibers in the light-collecting fiber bundle include a primary acid-resistant cladding and a secondary acid-soluble cladding that bonds individual fibers.

12. The method of claim 7 wherein the fiber bundle has a partial core size greater than 0.36, wherein the partial core size is core area divided by individual fiber area.

13. The method of claim 7 wherein the light-collecting fiber bundle is used for intracoronary laser speckle imaging.

14. The method of claim 7 wherein the fibers are situated within a contact-based intra-arterial catheter configured to reduce motion of a distal end of the fiber bundle during intracoronary imaging, and wherein the method further includes using the catheter for intracoronary imaging.

15. The method of claim 14 wherein the catheter is configured to reduce motion of a distal end of the fiber bundle during intracoronary laser speckle imaging.

16. The method of claim 14 wherein the catheter has a diameter no greater than 1.5 millimeters.

17. The method of claim 7 wherein the speckle imaging is intracoronary laser speckle imaging, and wherein the method further includes injecting a bolus of saline to dilute intervening blood and thereby diminish effects of the intervening blood on detection of the laser speckle pattern.

18. The method of claim 7 wherein the speckle imaging is intracoronary laser speckle imaging, and wherein the method further includes using a catheter with a motorized translation stage to control motion of the light-collecting fiber bundle along a coronary segment.

19. An apparatus for speckle imaging, comprising:
a light-delivery optical fiber configured to illuminate an anatomical structure with coherent light that scatters from the anatomical structure to form a speckle pattern; and
a light-collecting fiber bundle configured to collect scattered light and transmit the speckle pattern formed by the scattered light, wherein fibers in the light-collecting fiber bundle are separated by at least 3 times a width of at least one fiber core to reduce crosstalk between fiber;
wherein the apparatus is configured to diminish effects of intervening blood on detection of the laser speckle pattern by allowing no more than 200 μm of blood to flow between the light-collecting fiber bundle and the anatomical structure.

20. The apparatus of claim 19 wherein the light-collecting fiber bundle is further configured to reduce a measurable crosstalk down to no greater than 10 percent of collected light.

21. The apparatus of claim 20 wherein the light-collecting fiber bundle includes cladding, and wherein the crosstalk is measurable by illuminating one fiber in the light-collecting fiber bundle and detecting light leakage in the cladding and fibers adjacent to the illuminated fiber.

22. The apparatus of claim 19 further including a detector configured to detect and measure speckle patterns.

23. The apparatus of claim 19 wherein fibers in the light-collecting fiber bundle include a primary acid-resistant cladding and a secondary acid-soluble cladding that bonds individual fibers.

24. The apparatus of claim 19 wherein the fiber bundle has a partial core size no greater than 0.36, wherein the partial core size is core area divided by individual fiber area.

25. The apparatus of claim 19, wherein the fibers are situated within a contact-based intra-arterial catheter configured to maintain contact with vessel walls when the apparatus is imaging inside a blood vessel.

26. The apparatus of claim 25 wherein the catheter is configured to reduce motion of a distal end of the fiber bundle during intracoronary imaging.

27. The apparatus of claim 25 wherein the catheter has a diameter no greater than 1.5 millimeters.

28. The apparatus of claim 19 further including:
a catheter; and
a motorized, computer-controlled translation stage for translating the catheter along a coronary segment during intracoronary imaging.

29. The apparatus of claim 1, wherein the system includes a fluid injection system configured to inject a fluid into the coronary wall to dilute the intervening blood.

30. The apparatus of claim 1, further including an expandable basket having a prong configured to reduce a separation between the light-collecting fiber bundle and the coronary wall down to no greater than 200 μm.

31. The apparatus of claim 30, wherein the prong houses the light-collecting fiber bundle, and wherein the prong includes an optical window through which speckle patterns are imaged.

32. A system for intracoronary laser speckle imaging, comprising:
- a light-delivery optical fiber configured to illuminate a target confined by a coronary wall with laser light that scatters from the target to form a laser speckle pattern;
- a light-collecting fiber bundle configured to transmit the laser speckle pattern formed by the scattered light;
- a detector configured to detect the laser speckle pattern transmitted by the light-collecting fiber bundle; and
- a means for diminishing effects of intervening blood on detection of laser speckle patterns by allowing no more than the optical equivalent of a 200 µm layer of whole blood, in diluted or undiluted form, to flow between the light-collecting fiber bundle and the coronary wall.

33. The system of claim 32, wherein the means for diminishing effects of intervening blood includes a fluid injection system configured to inject a fluid into the coronary wall to dilute the flowing blood.

34. The system of claim 32, wherein the means for diminishing effects of intervening blood includes an expandable basket having a prong configured to reduce a separation between the light-collecting fiber bundle and the coronary wall down to no greater than 200 µm.

35. The system of claim 34, wherein the prong houses the light-collecting fiber bundle, and wherein the prong includes an optical window through which speckle patterns are imaged.

* * * * *

UNITED STATES PATENT AND TRADEMARK OFFICE
CERTIFICATE OF CORRECTION

PATENT NO. : 10,534,129 B2
APPLICATION NO. : 12/058279
DATED : January 14, 2020
INVENTOR(S) : Guillermo J. Tearney et al.

Page 1 of 1

It is certified that error appears in the above-identified patent and that said Letters Patent is hereby corrected as shown below:

In the Claims

Column 28, Claim 19, Line 23, "between fiber" should be --between fibers--.

Signed and Sealed this
Twenty-fifth Day of February, 2020

Andrei Iancu
*Director of the United States Patent and Trademark Office*